(12) United States Patent
Burkett

(10) Patent No.: US 9,878,142 B2
(45) Date of Patent: Jan. 30, 2018

(54) CONNECTION STRUCTURES FOR INTRAVASCULAR DEVICES AND ASSOCIATED SYSTEMS AND METHODS

(71) Applicant: Volcano Corporation, San Diego, CA (US)

(72) Inventor: David H. Burkett, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 587 days.

(21) Appl. No.: 14/341,511

(22) Filed: Jul. 25, 2014

(65) Prior Publication Data
US 2015/0032066 A1    Jan. 29, 2015

Related U.S. Application Data

(60) Provisional application No. 61/858,851, filed on Jul. 26, 2013.

(51) Int. Cl.
| | |
|---|---|
| *A61B 5/00* | (2006.01) |
| *A61M 39/10* | (2006.01) |
| *A61N 1/08* | (2006.01) |
| *A61B 5/0215* | (2006.01) |

(52) U.S. Cl.
CPC ...... *A61M 39/105* (2013.01); *A61M 39/1011* (2013.01); *A61B 5/02158* (2013.01); *A61M 2039/1022* (2013.01); *A61N 2001/083* (2013.01); *Y10T 29/49117* (2015.01)

(58) Field of Classification Search
CPC ....... A61B 5/2015; A61B 8/12; A61B 5/0538; A61M 25/09

USPC .......................................... 600/433, 434, 585
See application file for complete search history.

(56) References Cited

U.S. PATENT DOCUMENTS

| | | |
|---|---|---|
| 5,178,159 A | 1/1993 | Christian |
| 5,908,385 A | 6/1999 | Chechelski et al. |
| 6,032,061 A * | 2/2000 | Koblish ............... A61L 29/085 |
| | | 600/372 |
| 6,196,980 B1 | 3/2001 | Akerfeldt et al. |
| 8,277,386 B2 | 10/2012 | Ahmed et al. |

(Continued)

OTHER PUBLICATIONS

International Search Report and Written Opinion received in Patent Cooperation Treaty Application No. PCT/US2014/048234, dated Jul. 25, 2014, 14 pages.

*Primary Examiner* — Max Hindenburg
*Assistant Examiner* — Jonathan M Foreman

(57) ABSTRACT

Intravascular devices, systems, and methods are disclosed. In some embodiments, a method of assembling an intravascular device is provided that include positioning a first tubular member around a plurality of conductors and a core member such that the plurality of conductors and the core member are at least partially positioned within a lumen of the first tubular member, the first tubular member including an opening extending along a length of the first tubular member in communication with the lumen; positioning a first conductive member around the first tubular member; advancing a first of the plurality of conductors through the opening of the first tubular member, longitudinally between the first tubular member and the first conductive member, and through to a position adjacent to the first conductive member; and electrically coupling the first of the plurality of conductors to the first conductive member.

24 Claims, 17 Drawing Sheets

(56) References Cited

U.S. PATENT DOCUMENTS

| | | | |
|---|---|---|---|
| 8,600,518 B2* | 12/2013 | Meadows | A61N 1/05 600/373 |
| 8,858,468 B2* | 10/2014 | Sela | A61B 5/06 600/434 |
| 2007/0255145 A1 | 11/2007 | Smith et al. | |
| 2008/0119762 A1* | 5/2008 | Tateishi | A61M 25/09 600/585 |
| 2010/0262040 A1 | 10/2010 | Von Malmborg | |

\* cited by examiner

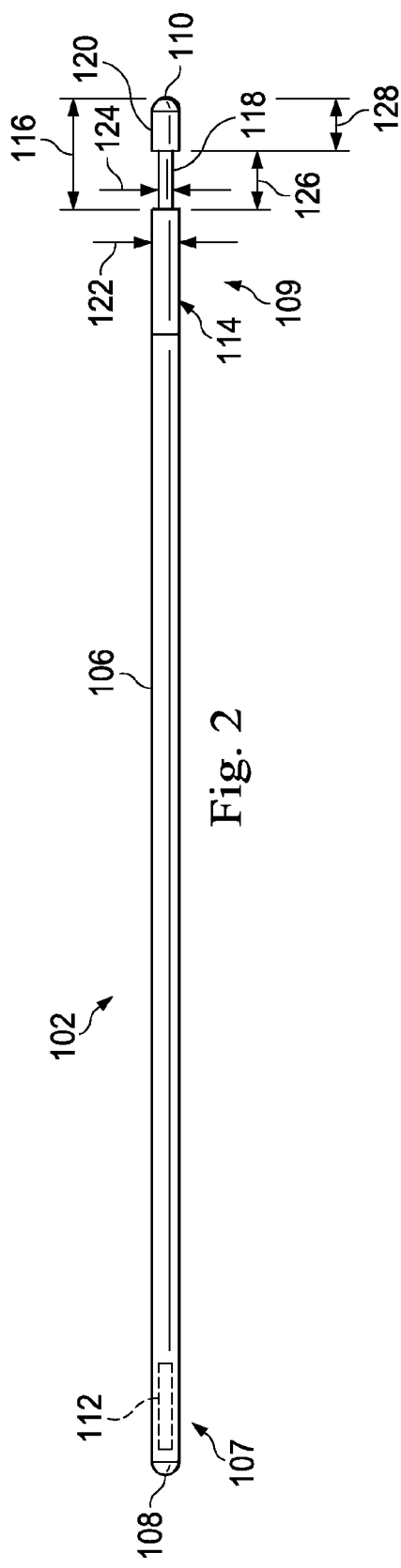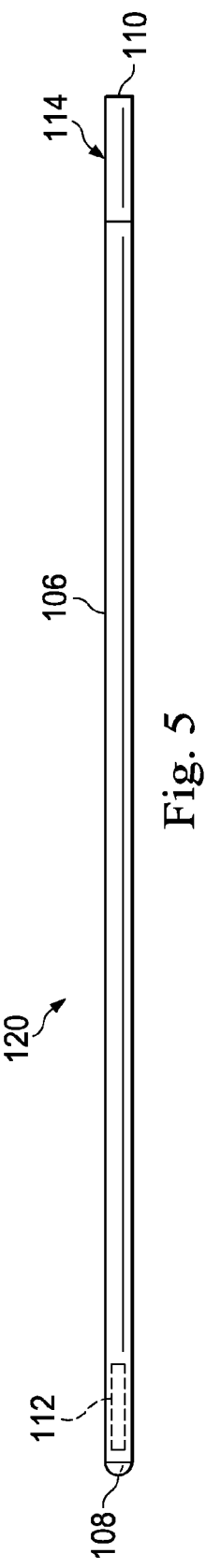

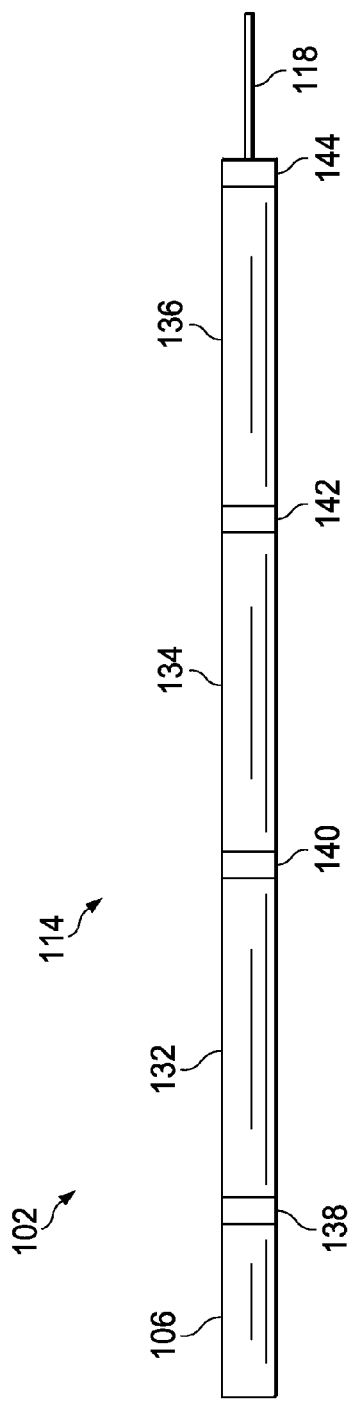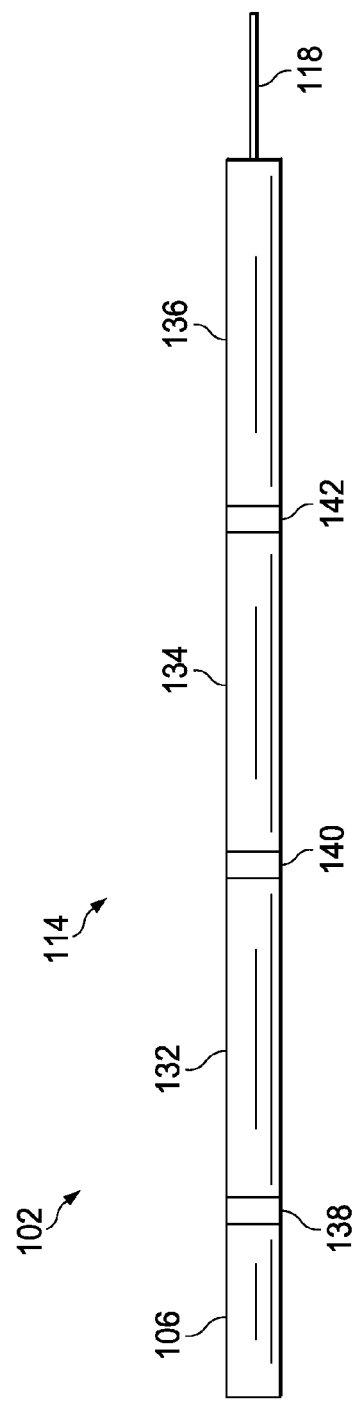

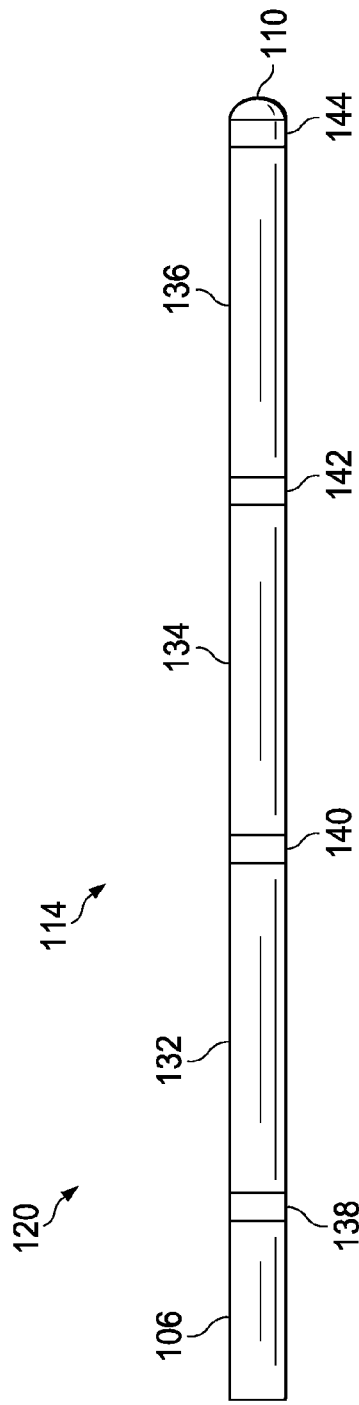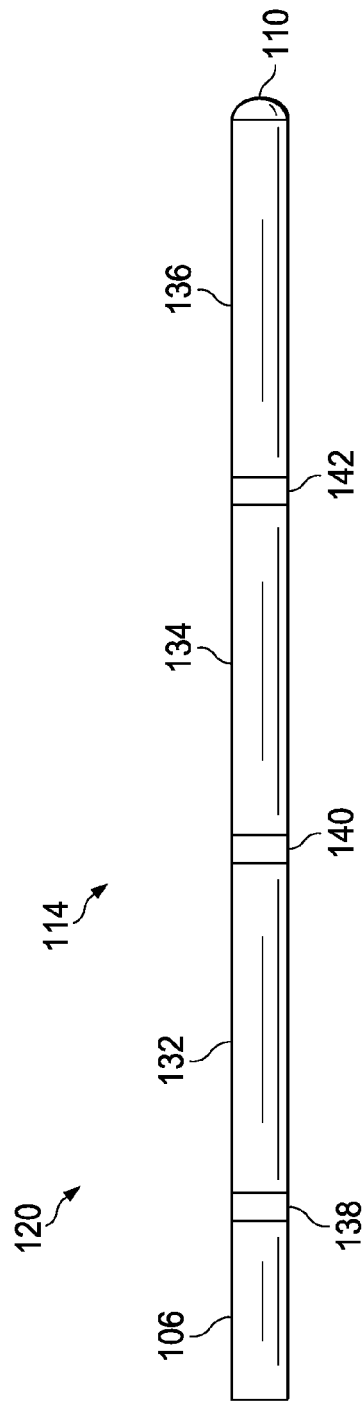

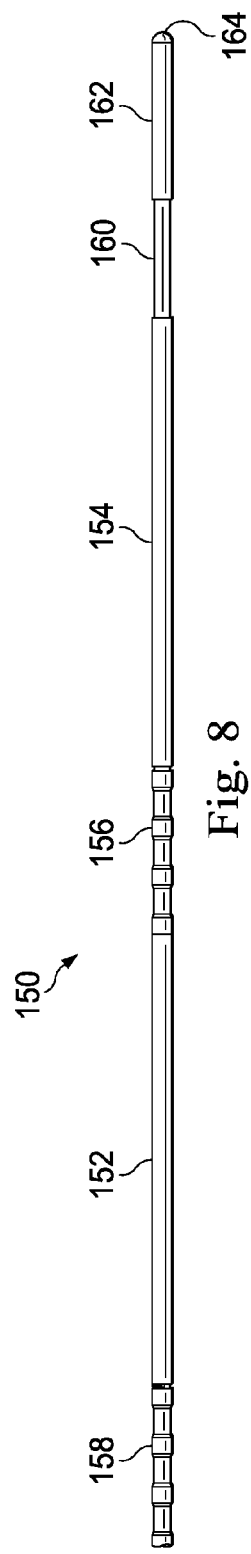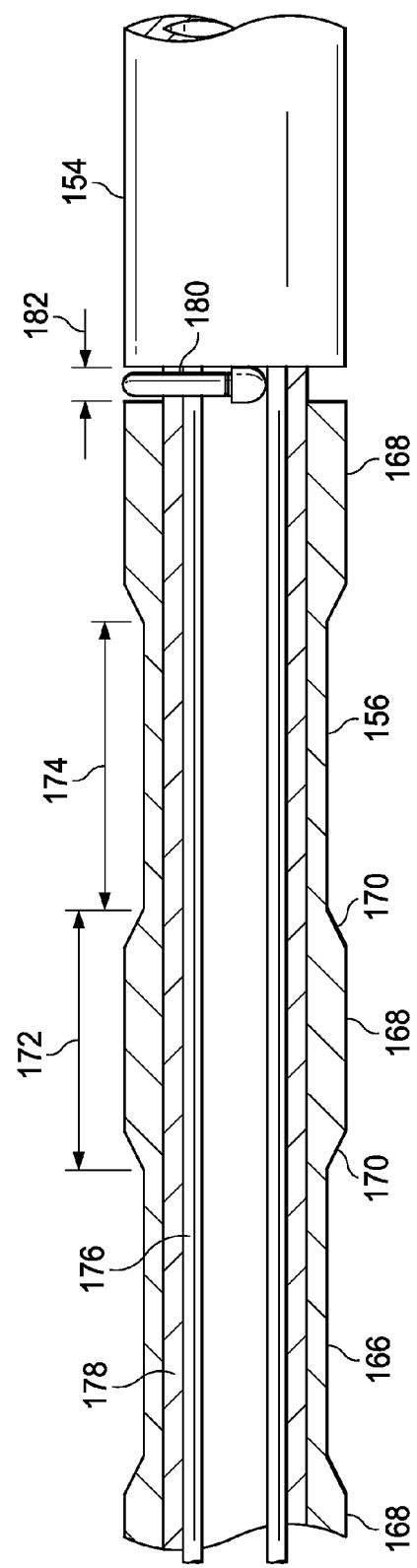

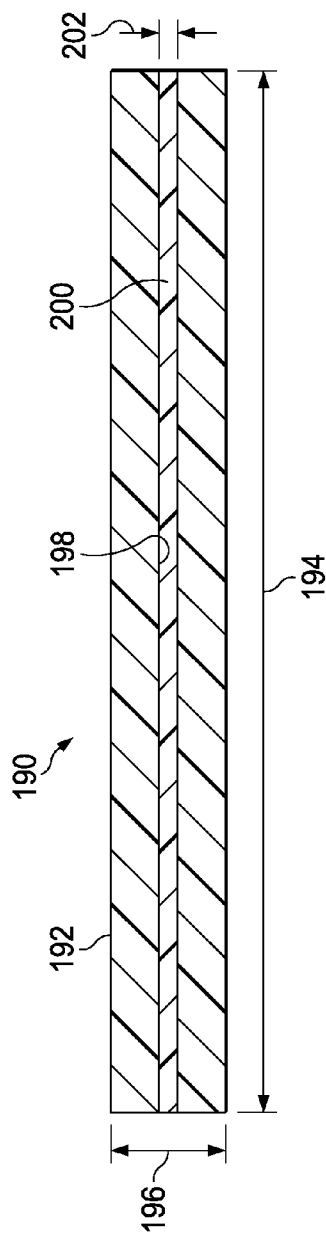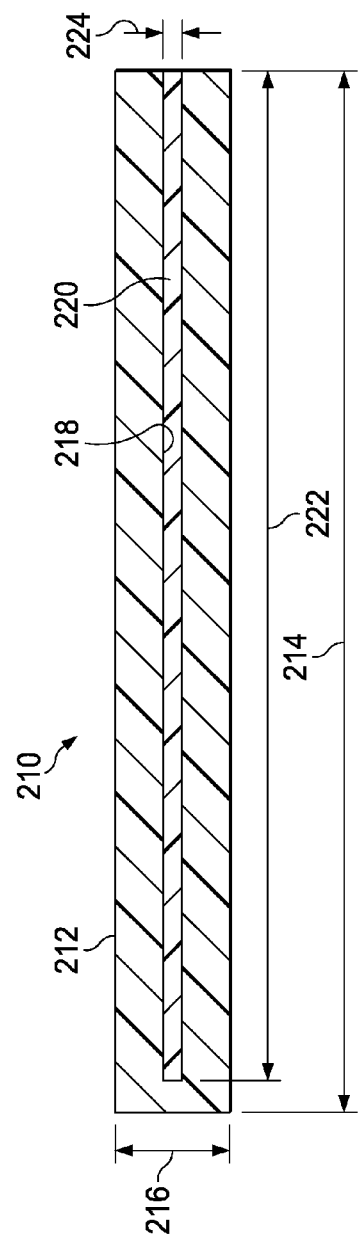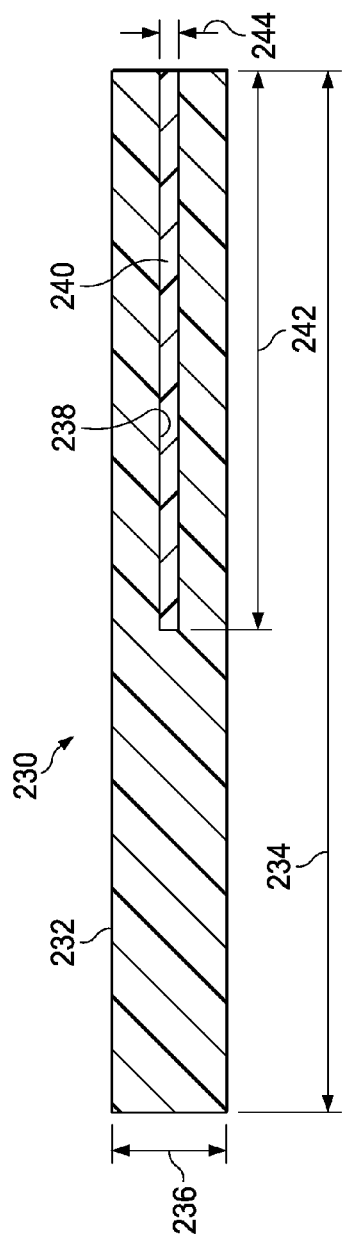

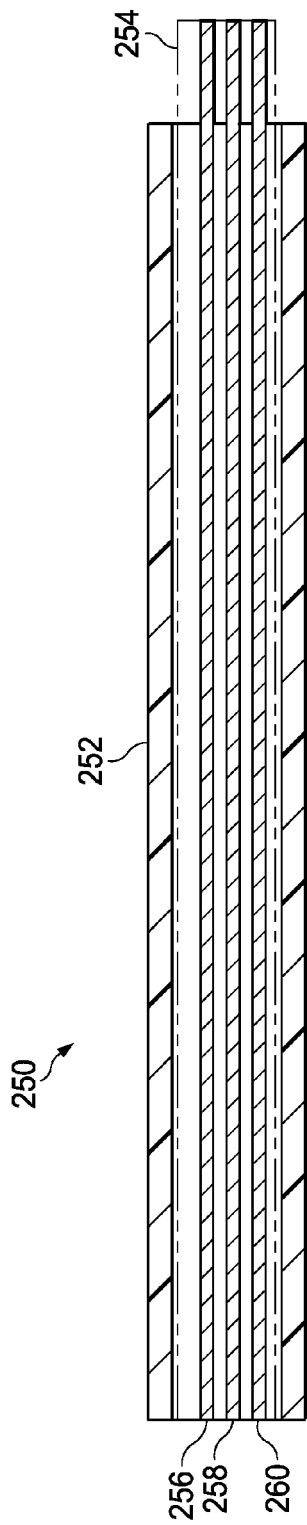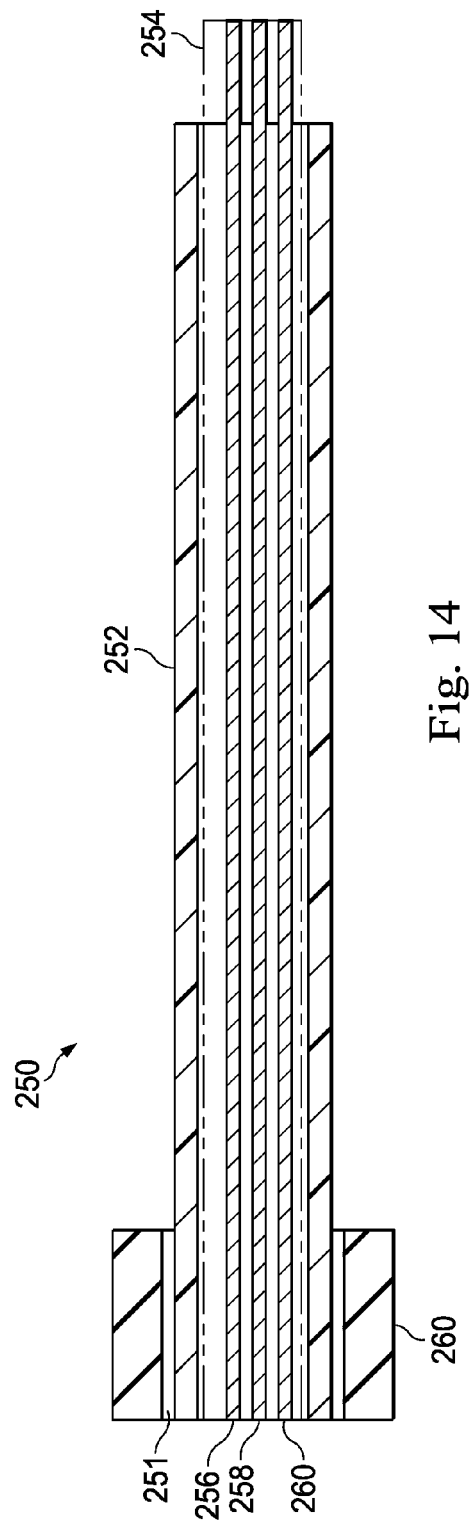

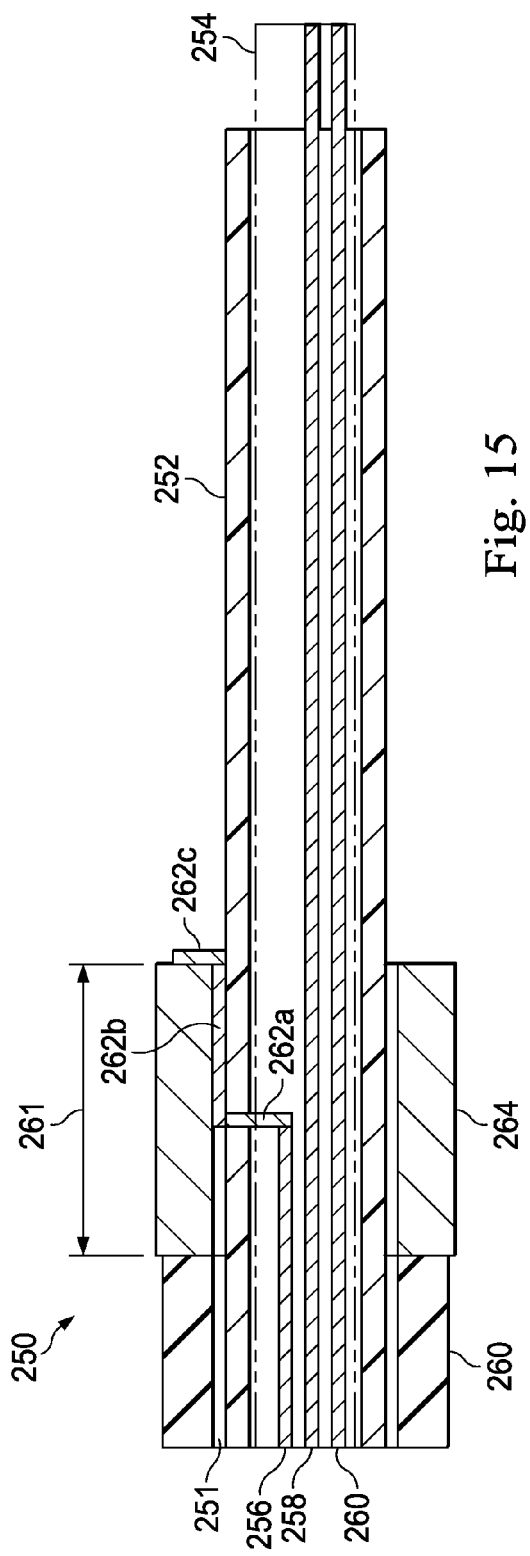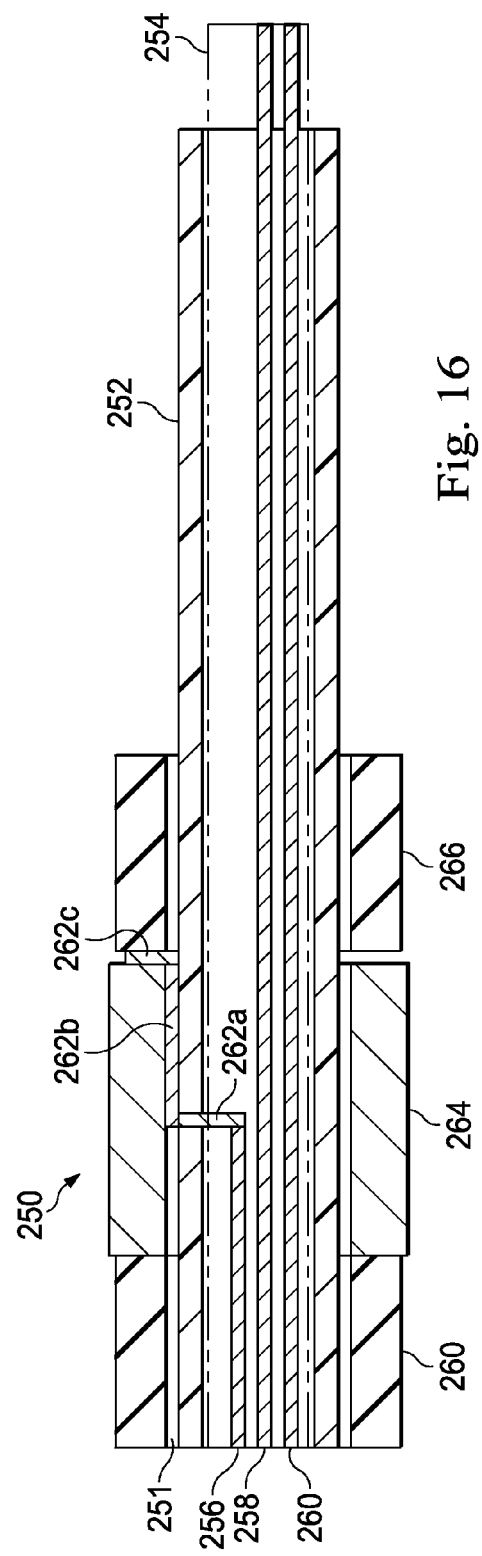

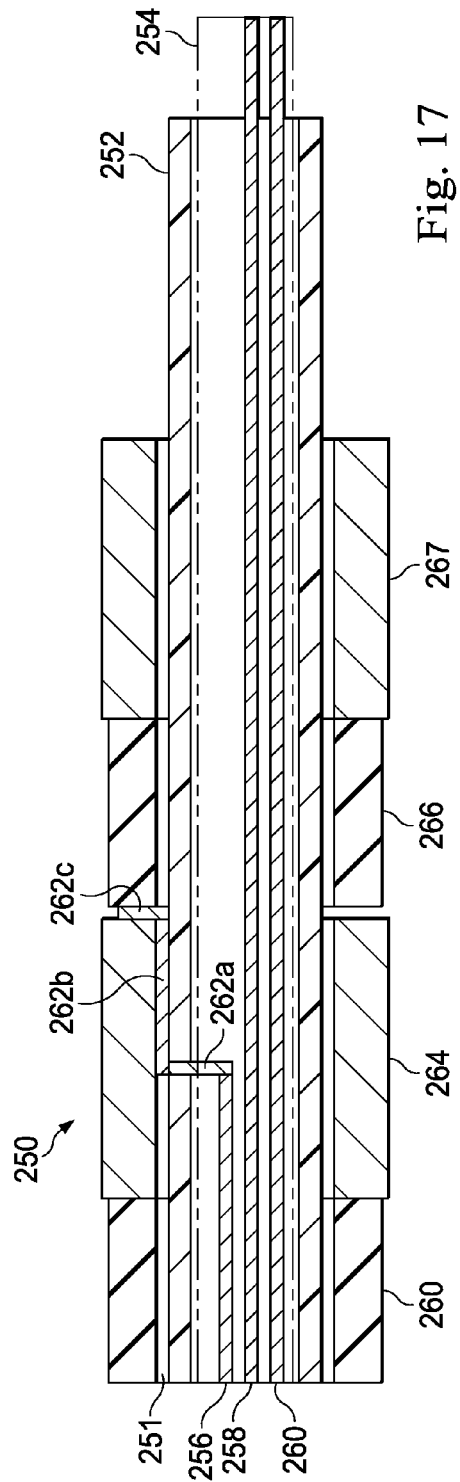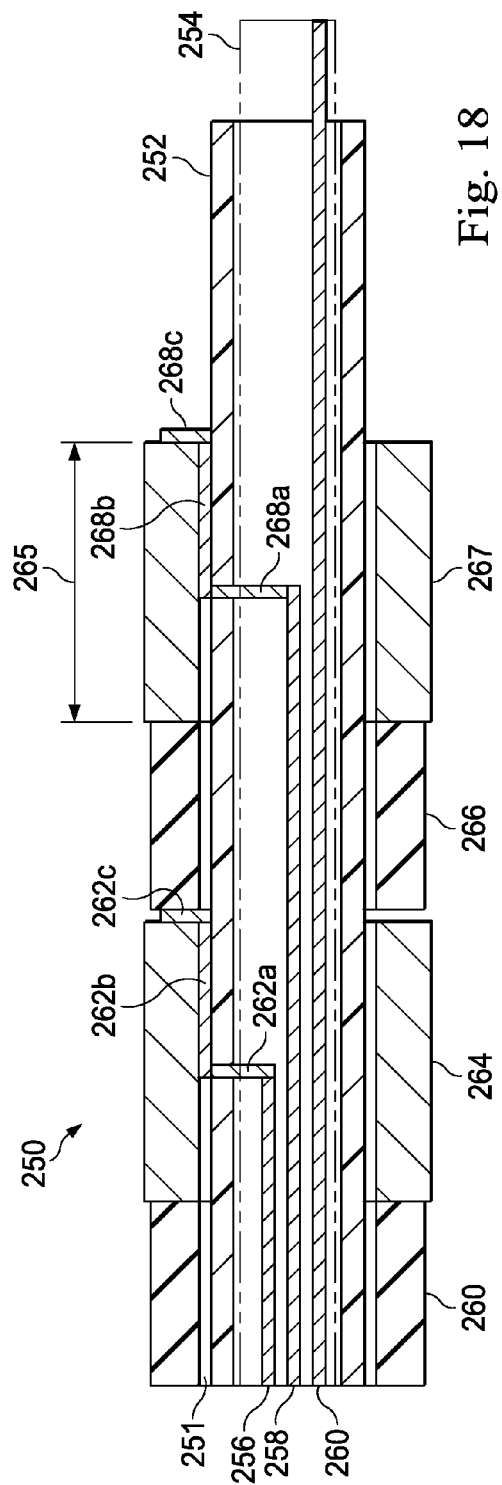

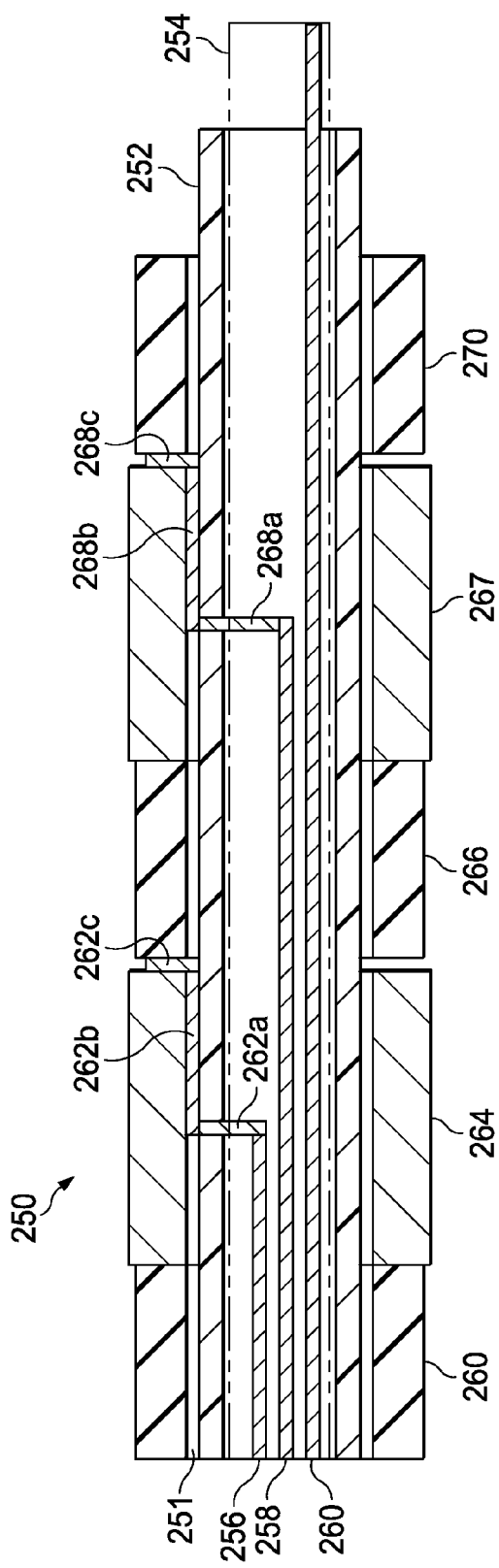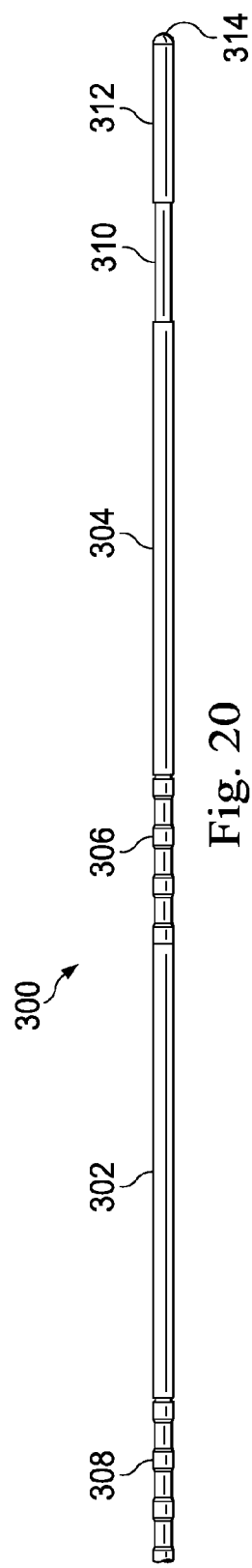
Fig. 19
Fig. 20

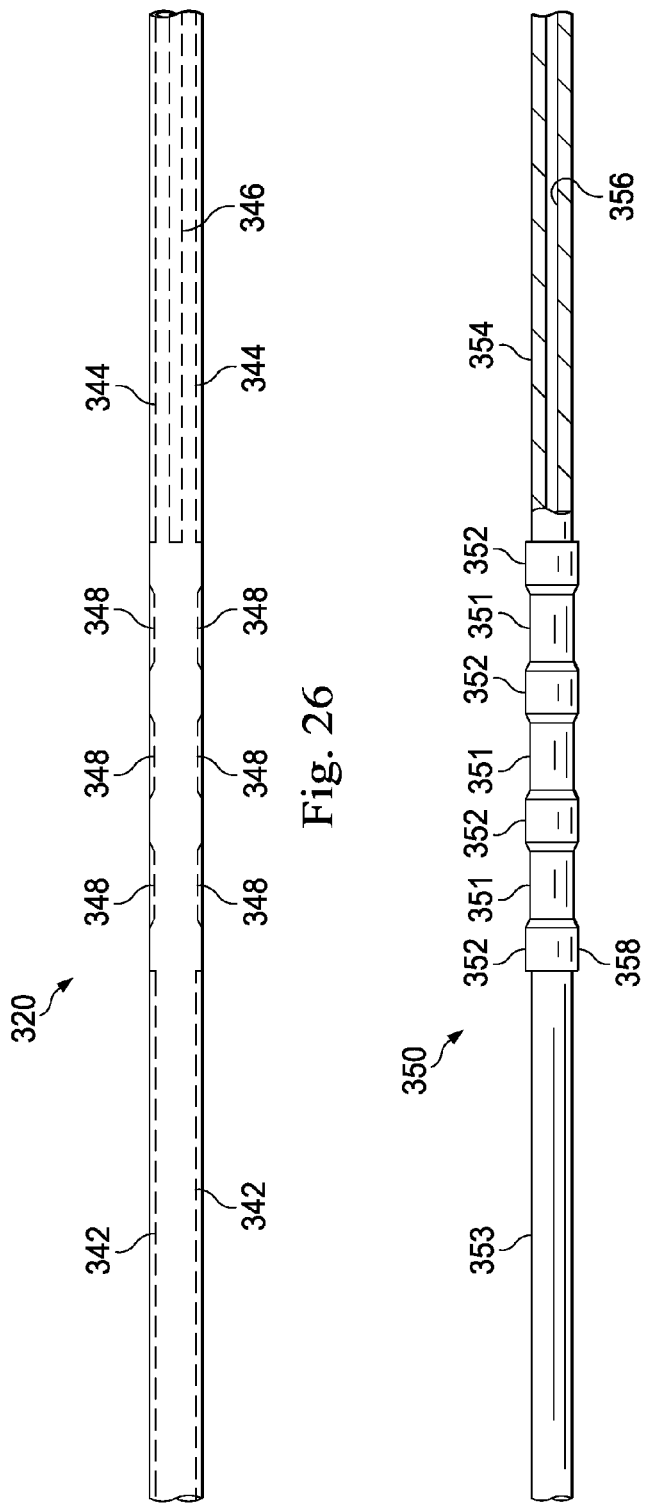
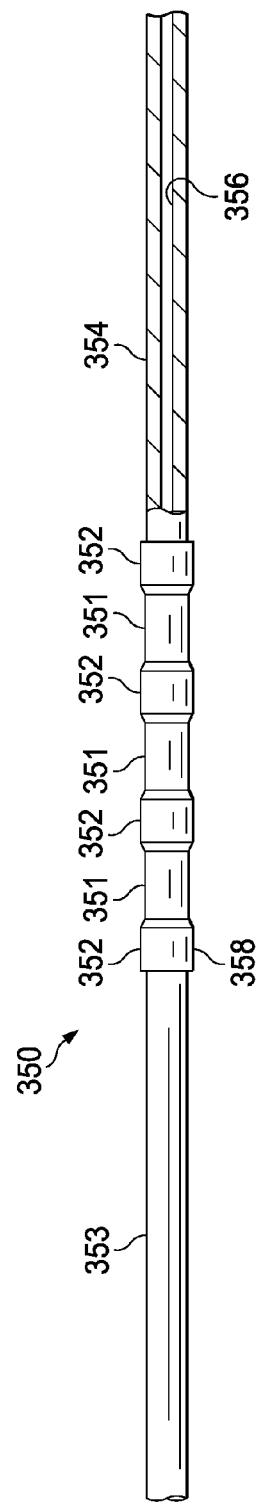
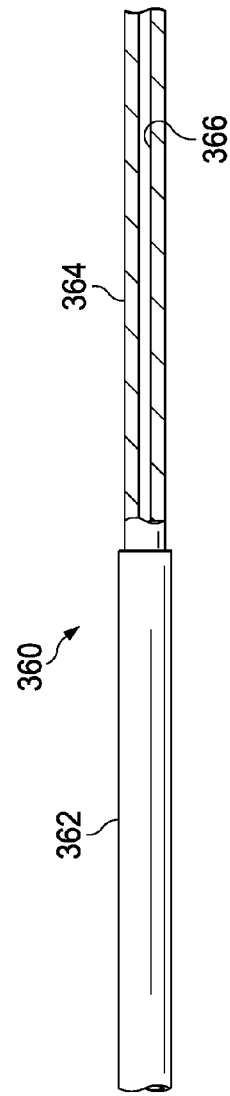
Fig. 26
Fig. 27
Fig. 28

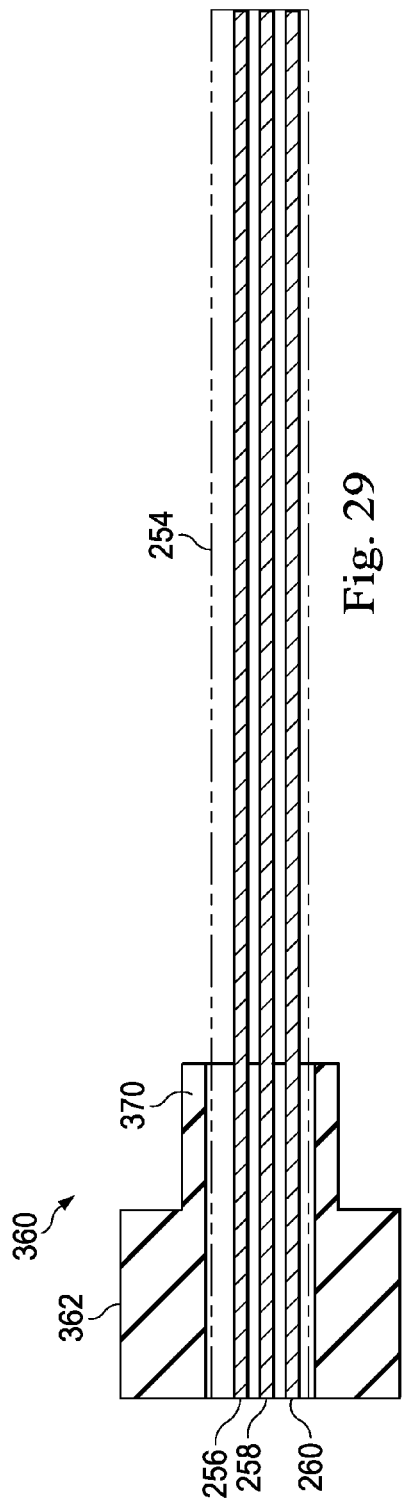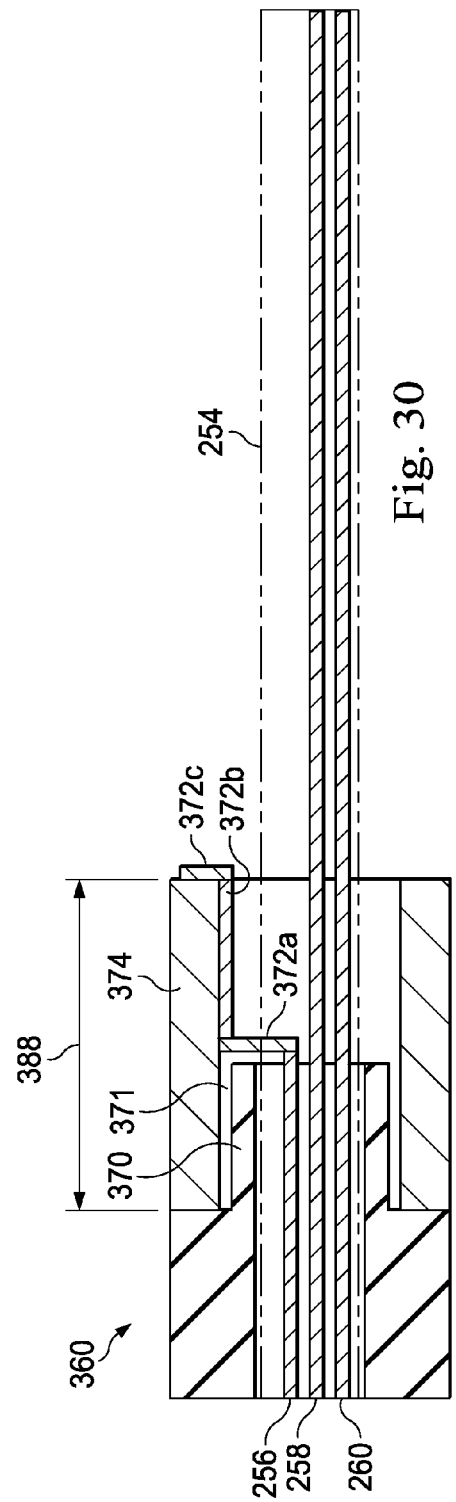

CONNECTION STRUCTURES FOR INTRAVASCULAR DEVICES AND ASSOCIATED SYSTEMS AND METHODS

CROSS REFERENCE TO RELATED APPLICATION

The present application claims priority to and the benefit of U.S. Provisional Patent Application No. 61/858,851 filed Jul. 26, 2013, which is hereby incorporated by reference herein in its entirety.

TECHNICAL FIELD

The present disclosure relates to intravascular devices, systems, and methods. In some embodiments, the intravascular devices are guidewires that include one or more electronic components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel. To date, guidewires containing pressure sensors or other electronic components have suffered from reduced performance characteristics compared to standard guidewires that do not contain electronic components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) is fragile and prone to kinking, which destroys the functionality of the guidewire. For this reason, surgeons are reluctant to remove the proximal connector from the guidewire during a procedure for fear of breaking the guidewire when reattaching the proximal connector. However, having the guidewire coupled to the proximal connector further limits the maneuverability and handling of the guidewire. Further, in some instances, the proximal connector portion of the guidewire is susceptible to short circuits that occur when a conductive fluid, such as blood or saline, infiltrates the proximal connector portion.

Accordingly, there remains a need for improved connectors and connector portions for use with intravascular devices (e.g., catheters and guidewires) that include one or more electronic components.

SUMMARY

Embodiments of the present disclosure are directed to intravascular devices, systems, and methods that include connection portions that are less susceptible to fluid penetration.

In some embodiments, the present disclosure relates to a proximal connection portion of a guidewire that includes one or more conductors extending in a non-linear manner from an inner lumen of a tubular insulating member to a position adjacent to an outer conductive band. For example, in some implementations one or more conductors of the guidewire extend vertically (at least partially transverse to the length of the guidewire) through an opening in an inner tube of the guidewire, horizontally (at least partially along the length of the guidewire) between the inner tube and a conductive band of the guidewire, and vertically (at least partially transverse to the length of the guidewire) through to a position next to the conductive band.

In some embodiments, methods of assembling an intravascular device are provided. In one embodiment, the method includes positioning a first tubular member around a plurality of conductors and a core member such that the plurality of conductors and the core member are at least partially positioned within a lumen of the first tubular member, the first tubular member including an opening extending along a length of the first tubular member in communication with the lumen; positioning a first conductive member around the first tubular member; advancing a first of the plurality of conductors through the opening of the first tubular member, longitudinally between the first tubular member and the first conductive member, and through to a position adjacent to the first conductive member; and electrically coupling the first of the plurality of conductors to the first conductive member. In some instances, the method further includes positioning a first insulating member around the first tubular member adjacent to the first conductive member; positioning a second conductive member around the first tubular member adjacent to the first insulating member such that the first insulating member is positioned between the first and second conductive members; and electrically coupling a second of the plurality of conductors to the second conductive member. In the regard, the second of the plurality of conductors is advanced through the opening of the first tubular member, longitudinally between the first tubular member and the second conductive member, and through to a position adjacent to the second conductive member.

In some embodiments, an intravascular device is provided. In one embodiment, the intravascular device includes a tubular member positioned around a plurality of conductors and a core member such that the plurality of conductors and the core member are at least partially positioned within a lumen of the tubular member; a first conductive member positioned around the tubular member, wherein a first of the plurality of conductors is electrically coupled to the first conductive member and extends longitudinally between the tubular member and the first conductive member and through to a position adjacent to the first conductive member; a first insulating member positioned around the tubular member adjacent to the first conductive member; and a second conductive member positioned around the tubular member adjacent to the first insulating member such that the first insulating member is positioned between the first and second conductive members, wherein a second of the plurality of conductors is electrically coupled to the second conductive member. In some instances, the opening extends along an entire length of the tubular member. In other instances, the opening extends along only a portion of the length of the tubular member. In some implementations, the intravascular device includes a second insulating member positioned around the tubular member adjacent to the second conductive member and a third conductive member positioned around the tubular member adjacent to the second insulating member such that the second insulating member is positioned between the second and third conductive members.

In another embodiment, the intravascular device includes a first insulating member positioned around a plurality of conductors and a core member such that the plurality of conductors and the core member are at least partially positioned within a lumen of the first insulating member, the first insulating member having a first portion with a first diameter, a second portion with a second diameter less than the first diameter, and an opening extending along a length of the first insulating member in communication with the lumen; and a first conductive member positioned around the second portion of the first insulating member, wherein a first of the plurality of conductors is electrically coupled to the first conductive member and extends through the opening in the first insulating member, longitudinally between the first insulating member and the first conductive member, and through to a position adjacent to the first conductive member. In some instances, the opening of the first insulating member extends along only a portion of the length of the first insulating member. In some particular instances, the opening of the first insulating member extends along the second portion of the first insulating member. In some embodiments, the first conductive member has an outer diameter equal to the first diameter.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 2 is a diagrammatic side view of an intravascular device of the intravascular system of FIG. 1 according to an embodiment of the present disclosure.

FIG. 3 is a diagrammatic side view of a proximal connector portion of the intravascular device of FIG. 2 according to an embodiment of the present disclosure.

FIG. 4 is a diagrammatic side view of a proximal connector portion of an intravascular device of FIG. 2 similar to that of FIG. 3, but illustrating another embodiment of the present disclosure.

FIG. 5 is a diagrammatic side view of an intravascular device of the intravascular system of FIG. 1 similar to that of FIG. 2, but illustrating another embodiment of the present disclosure.

FIG. 6 is a diagrammatic side view of a proximal connector portion of the intravascular device of FIG. 5 according to an embodiment of the present disclosure.

FIG. 7 is a diagrammatic side view of a proximal connector portion of an intravascular device of FIG. 5 similar to that of FIG. 6, but illustrating another embodiment of the present disclosure.

FIG. 8 is a diagrammatic side view of a proximal connector portion of an intravascular device according to an embodiment of the present disclosure.

FIG. 9 is a diagrammatic partial cross-sectional side view of the proximal connector portion of FIG. 8.

FIG. 10 is a diagrammatic side view of a component of the proximal connector portion of FIGS. 8 and 9 according to an embodiment of the present disclosure.

FIG. 11 is a diagrammatic side view of a component of the proximal connector portion of FIGS. 8 and 9 similar to that of FIG. 10, but illustrating another embodiment of the present disclosure.

FIG. 12 is a diagrammatic side view of a component of the proximal connector portion of FIGS. 8 and 9 similar to that of FIGS. 10 and 11, but illustrating yet another embodiment of the present disclosure.

Collectively, FIGS. 13-19 illustrate various aspects of assembling a proximal connector portion as illustrated in FIGS. 8 and 9 according to an exemplary embodiment of the present disclosure.

FIG. 13 is a diagrammatic cross-sectional side view showing a component, such as one of the components of FIGS. 10-12, being positioned over a core wire and a plurality of conductors.

FIG. 14 is a diagrammatic cross-sectional side view showing an insulating element being positioned over the component of FIG. 13.

FIG. 15 is a diagrammatic cross-sectional side view showing a conductive element being positioned over the component of FIG. 13, and one of the plurality of conductors being passed through an opening the component of FIG. 13 and electrically coupled to the conductive element.

FIG. 16 is a diagrammatic cross-sectional side view showing another insulating element being positioned over the component of FIG. 13 and positioned adjacent to the conductive element of FIG. 15.

FIG. 17 is a diagrammatic cross-sectional side view showing another conductive element being positioned over the component of FIG. 13 and positioned adjacent to the insulating element of FIG. 16.

FIG. 18 is a diagrammatic cross-sectional side view showing another of the plurality of conductors being passed through an opening the component of FIG. 13 and electrically coupled to the conductive element of FIG. 17.

FIG. 19 is a diagrammatic cross-sectional side view showing another insulating element being positioned over the component of FIG. 13 and positioned adjacent to the conductive element of FIG. 17.

FIG. 20 is a diagrammatic side view of a proximal connector portion of an intravascular device according to another embodiment of the present disclosure.

FIG. 26 is a diagrammatic side view of the element of FIG. 23 with markings showing portions of the element that will be removed to form a component of the proximal connector portion of FIGS. 20-22 according to another embodiment of the present disclosure.

FIG. 27 is a diagrammatic side view of a component of the proximal connector portion of FIGS. 20-22 formed from the element of FIG. 23 according to the markings shown in FIG. 26.

FIG. 28 is a diagrammatic side view of a component of the proximal connector portion of FIGS. 20-22 formed from the element of FIG. 23 according to another embodiment of the present disclosure.

Collectively, FIGS. 29-33 illustrate various aspects of assembling a proximal connector portion similar to the embodiment illustrated in FIGS. 20-22 according to an exemplary embodiment of the present disclosure.

FIG. 29 is a diagrammatic cross-sectional side view showing a component, such as one of the components of FIGS. 25, 27, and/or 28, being positioned over a core wire and a plurality of conductors.

FIG. 30 is a diagrammatic cross-sectional side view showing a conductive element being positioned over a portion of the component of FIG. 29, and one of the plurality of conductors being passed through an opening the component of FIG. 29 and electrically coupled to the conductive element.

FIG. 31 is a diagrammatic cross-sectional side view showing another component, such as one of the components of FIGS. 25, 27, and/or 28, being positioned adjacent to the conductive element of FIG. 30 such that a portion of the conductive element is positioned over the component.

FIG. 32 is a diagrammatic cross-sectional side view showing a conductive element being positioned over a portion the component of FIG. 31, and one of the plurality of conductors being passed through an opening the component of FIG. 31 and electrically coupled to the conductive element.

FIG. 33 is a diagrammatic cross-sectional side view showing another component, such as one of the components of FIGS. 25, 27, and/or 28, being positioned adjacent to the conductive element of FIG. 32 such that a portion of the conductive element is positioned over the component.

DETAILED DESCRIPTION

Figure 1:
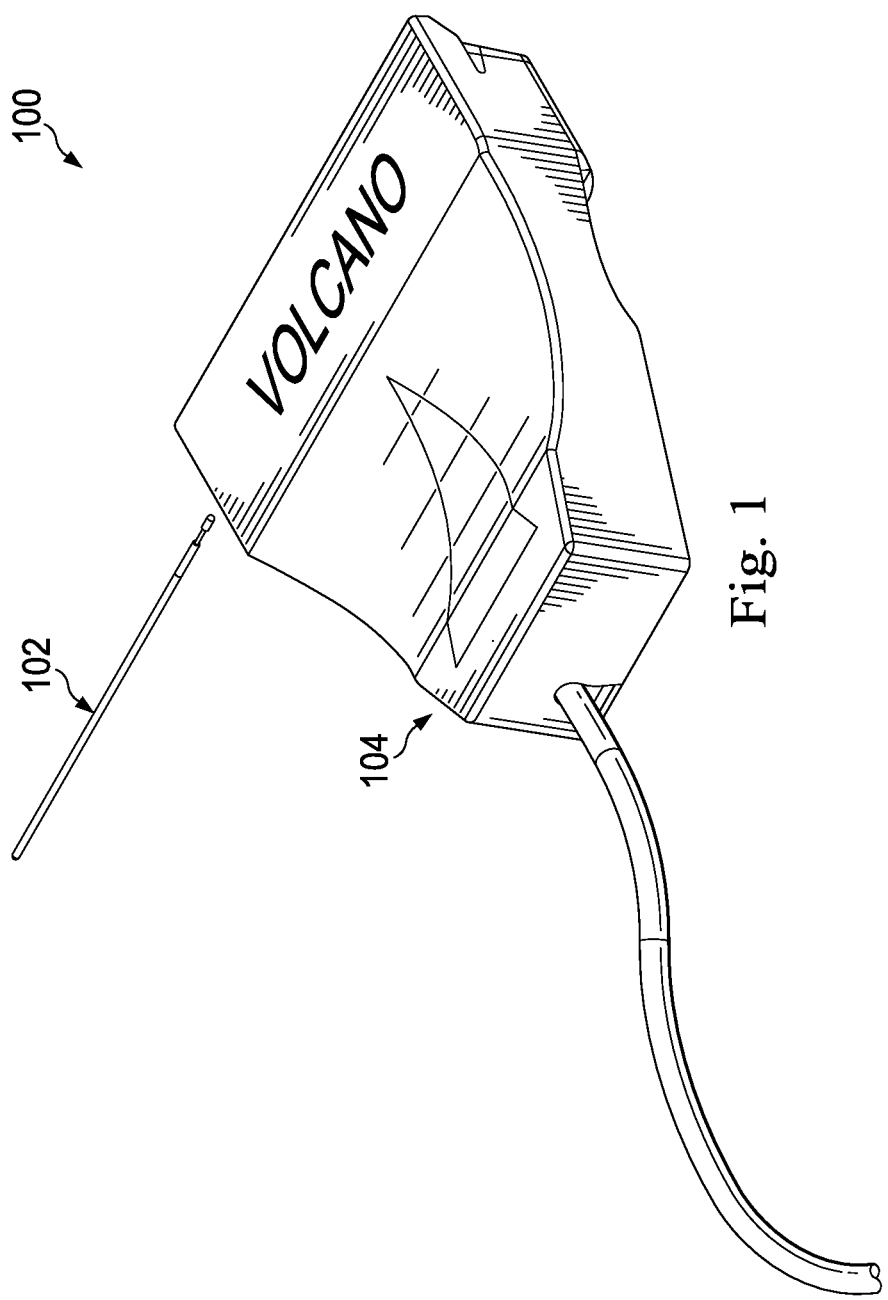
FIG. 1 is a diagrammatic perspective view of an intravascular system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a minor, a prism, an ablation element, an fro electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized. Further, in some instances the flexible elongate member includes multiple electronic, optical, and/or electro-optical components (e.g., pressure sensors, temperature sensors, imaging elements, optical fibers, ultrasound transducers, reflectors, mirrors, prisms, ablation elements, fro electrodes, conductors, etc.).

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is an intravascular system 100 according to an embodiment of the present disclosure. In that regard, the intravascular system includes an intravascular device 102 and a connector 104. Referring now to FIG. 2, a side view of the intravascular device 102 is provided according to an embodiment of the present disclosure. As shown, the intravascular device 102 includes a flexible elongate member 106 having a distal portion 107 adjacent a distal end 108 and a proximal portion 109 adjacent a proximal end 110. A component 112 is positioned within the distal portion 107 of the flexible elongate member 106 proximal of the distal tip 108. Generally, the component 112 is representative of one or more electronic, optical, or electro-optical components. In that regard, the component 112 is a pressure sensor, a temperature sensor, an imaging element, an optical fiber, an ultrasound transducer, a reflector, a minor, a prism, an ablation element, an fro electrode, a conductor, and/or combinations thereof. The specific type of component or combination of components can be selected based on an intended use of the intravascular device. In some instances, the component 112 is positioned less than 10 cm, less than 5, or less than 3 cm from the distal tip 108. In some instances, the component 112 is positioned within a housing of the intravascular device 102. In that regard, the housing is a separate component secured to the flexible elongate member 106 in some instances. In other instances, the housing is integrally formed as a part of the flexible elongate member 106. In some embodiments, the flexible elongate member 106 comprises a stainless steel hypotube. Further, in some embodiments all or a portion of the flexible elongate member 106 is covered with a hydrophilic or hydrophobic coating. In some particular embodiments, a polytetrafluoroethylene (PTFE) coating is utilized.

The intravascular device 102 also includes a connection portion 114 adjacent the proximal portion 109 of the device. In that regard, the connection portion 114 is spaced from the proximal end 110 of the flexible elongate member 106 by a distance 116. Generally, the distance 116 is between 0% and 50% of the total length of the flexible elongate member 106. While the total length of the flexible elongate member can be any length, in some embodiments the total length is between about 1300 mm and about 4000 mm, with some specific embodiments having a length of 1400 mm, 1900 mm, and 3000 mm. In some instances the connection portion 114 is spaced from the proximal end 110 between about 0 mm and about 1400 mm. In some specific embodiments, the connection portion 114 is spaced from the proximal end by a distance of 0 mm, 300 mm, and 1400 mm. Accordingly, in some instances the connection portion 114 is positioned at the proximal end 110. In some such embodiments, one or more aspects of the engagement and alignment features of the intravascular device 102 discussed below are positioned distal of the of the connection portion 114 instead of proximal of the connection portion 114 as shown in the embodiment of FIG. 2.

In that regard, in the illustrated embodiment of FIG. 2 the intravascular device 102 includes a section 118 extending proximally from the connection portion 114 to another section 120 that extends to proximal end 110. In the illustrated embodiment, the section 120 is rounded to proximal end 110. In other embodiments, the section 120 has a tapered, arcuate, and/or other changing profile as it extends proximally to proximal end 110. In that regard, in some instances the outer profile and/or diameter of the section 120 reduces as it extends proximally to proximal end 110 such that the reduced profile and/or diameter of the proximal end facilitates easier introduction of one or more other instruments over the intravascular device. In other embodiments, the section 120 has a constant profile as it extends proximally to proximal end 120.

As shown, the connection portion 114 has a diameter 122 (or other similar measurement for outer cross-section profiles for non-circular cross-sectional embodiments) while section 118 has a diameter 124 (again, or other similar measurement for outer cross-section profiles for non-circular cross-sectional embodiments). The diameter 124 of section 118 is different than the diameter 122 of connection portion 114. In that regard, the different sizes of the diameters 122, 124 creates a structure that is configured to facilitate alignment and/or connection of the intravascular device 102 to a connector, such as connector 104. In the illustrated embodiment, the diameter 124 of section 118 is less than the diameter 122 of the connection portion 114. In some embodiments, the diameter 124 of section 118 is between about 40% and about 80% of diameter 122, with some particular embodiments being about 42%, 64%, and/or other percentage of diameter 122. In that regard, in some embodiments the diameter 122 of connection portion 114 is between about 0.0178 mm and about 3.0 mm, with some particular embodiments being 0.3556 mm (0.014") and 0.4572 mm (0.018"). Accordingly, in some embodiments the diameter 124 of section 118 is between about 0.007 mm and about 2.4 mm, with some particular embodiments being 0.15 mm, 0.19 mm, 0.23 mm, and 0.29 mm. In the illustrated embodiment, the section 120 has a diameter that is approximately equal to diameter 122 and, therefore, greater than diameter 124. However, in other embodiments, section 120 has a diameter that is greater than diameter 122, less than diameter 122, greater than diameter 124, equal to diameter 124, and/or less than diameter 124. In some embodiments, section 118 is a section of a core wire extending through the connection portion 114.

As shown in FIG. 2, the section 118 extends proximally from connection portion 114 a distance 126, while section 120 extends proximally from section 118 to proximal end 110 a distance 128. Together, distances 126 and 128 equal the distance 116 that the connection portion 114 is spaced from the proximal end 110 of the intravascular device 102. In some instances, the distance 126 of is between about 0.508 mm (0.020") and about 2.54 mm (0.10"), with some particular embodiments being 0.762 mm (0.030"), 1.016 mm (0.040"), and 1.524 mm (0.060"). Further, while the transition between connection portion 114 and section 118 and the transition between section 118 and section 120 are shown as being stepped in the illustrated embodiments, in other embodiments the transitions are tapered and/or otherwise make a gradual change in outer diameter along the length of the intravascular device. In some embodiments, use of tapered and/or gradual transitions results in the proximal portion of the intravascular device 102 not having any sharp edges. In some implementations, the use of tapered and/or gradual transitions for one or both of the transitions between section 118 and either the connection portion 114 or section 120 makes cleaning the proximal portion of the device (e.g., to remove any liquids or other unwanted materials on the surface of the proximal portion of the intravascular device) easier. In some instances, sections 118 and 120 are formed as a separate assembly or component and subsequently joined to the connection portion 114 via suitable techniques, such as using solder, adhesive, mechanical connections, and/or combinations thereof.

The connection portion 114 is configured to facilitate communication between the intravascular device 102 and another device. More specifically, in some embodiments the connection portion 114 is configured to facilitate communication of data obtained by the component 112 to another device, such as a computing device or processor. Accordingly, in some embodiments the connection portion 114 is an electrical connector. In such instances, the connection portion 114 is configured to provide an electrical connection to one or more electrical conductors that extend along the length of the flexible elongate member 102 and are electrically coupled to the component 112. In some instances, the connection portion 114 includes one or more electrical connectors as described in U.S. Patent Application No. 61/665,697, titled "INTRAVASCULAR DEVICES, SYSTEMS, AND METHODS" and filed Jun. 28, 2012, which is hereby incorporated by reference in its entirety. In other embodiments, the connection portion 114 includes an optical connector. In such instances, the connection portion 114 provides an optical connection to one or more optical communication pathways (e.g., fiber optic cable) that extend along the length of the flexible elongate member 106 and are optically coupled to the component 112. Further, in some embodiments the connection portion 114 provides both electrical and optical connections to both electrical conductor(s) and optical communication pathway(s) coupled to the component 112. In that regard, it should again be noted that component 112 is comprised of a plurality of elements in some instances. In some instances, the connection portion 114 is configured to provide a physical connection to another device, either directly or indirectly. In other instances, the connection portion 114 is configured to facilitate wireless communication between the intravascular device 102 and another device. Generally, any current or future developed wireless protocol(s) may be utilized. In yet other instances, the connection portion 114 facilitates both physical and wireless connection to another device.

As noted above, in some instances the connection portion 114 provides a connection between the component 112 of the intravascular device 102, 120 and an external device. Accordingly, in some embodiments one or more electrical conductors, one or more optical pathways, and/or combinations thereof extend along the length of the flexible elongate member 106 between the connection portion 114 and the component 112 to facilitate communication between the connection portion 114 and the component 112. Generally, any number of electrical conductors, optical pathways, and/or combinations thereof can extend along the length of the flexible elongate member 106 between the connection portion 114 and the component 112. In some instances, between one and ten electrical conductors and/or optical pathways extend along the length of the flexible elongate member 106 between the connection portion 114 and the component 112. For the sake of clarity and simplicity, the embodiments of the present disclosure described below include three electrical conductors and, therefore, the connection portion 114 is described as having three separate electrical connections corresponding to the three electrical conductors.

For example, as shown in FIG. 3, in some instances the connection portion 114 includes conductive portions 132, 134, and 136 that are separated from one another and the main body of the flexible elongate member 106 by insulating portions 138, 140, 142, and 144. In that regard, the conductive portions 132, 134, and 136 are formed of a conductive material and are portions of a hypotube, a coil, and/or combinations thereof in some instances. It is understood that the total number of communication pathways and/or the number of electrical conductors and/or optical pathways is different in other embodiments and, therefore, the number of conductive portions (or optical connectors) included in connection portion is different as well. More specifically, the number of communication pathways and the number of electrical conductors and optical pathways extending along the length of the flexible elongate member 106 is determined by the desired functionality of the component 112 and the corresponding elements that define component 112 to provide such functionality. As a result, the number and type of connections provided by connection portion 114 are likewise determined by the desired functionality of the component 112, the corresponding elements that define component 112 to provide such functionality, and the communication needs for such elements. Further still, in some instances, one or more of the insulating portions 138, 140, 142, and 144 is omitted. For example, as shown in the exemplary embodiment of FIG. 4, insulating portion 144 has been omitted.

As noted above, in some instances the connection portion 114 is not spaced from the proximal end 110. For example, FIG. 5 illustrates an intravascular device 120 where the connection portion is positioned at the proximal end 110 of the intravascular device. In such embodiments, the proximal end 110 of the intravascular device 120 may be defined by an insulating element (as shown by insulating portion 144 in FIG. 6) or a conductive element (as shown by conductive portion 136 in FIG. 7). It should also be noted that while the arrangements of FIGS. 3, 4, 5, and 6 illustrate an insulating portion 138 as being positioned between the flexible elongate member 106 and the conductive portion 132, in some instances the conductive portion 132 is positioned immediately adjacent to the elongate member without insulating portion 138. Accordingly, the various embodiments and associated methods of forming connection portions for intravascular devices as discussed below may be implemented using any combination of the arrangement of features described above with respect to FIGS. 1-7.

Referring now to FIGS. 8 and 9, shown therein are aspects of a connector portion 150 of an intravascular device according to an embodiment of the present disclosure. As shown in FIG. 8, the connector portion 150 includes conductive portions 152, 154 and insulating portions 156, 158. In that regard, the insulating portion 156 separates the conductive portion 152 from the conductive portion 154. In some instances, the insulating portion 158 separates the conductive portion 152 from one or more other conductive portions (not shown) of the connector portion 150. A section 160 extending proximally from the connector portion 150 to another section 162 that extends to a proximal end 164. The sections 160, 162 have structures and arrangements as described above with respect to sections 118, 120 in some instances.

Referring now to FIG. 9, shown therein is a partial cross-sectional side view of part of the proximal connector portion 150. As shown, the insulating portion 156 includes an outer surface 166. A plurality of projections 168 extend from the outer surface 166. Generally, the connector portion 150 can include any number of projections 168 (or omit the projections entirely), but in some embodiments the connector portion 150 includes between 0 and 20 projections, with some particular embodiments having 0, 1, 5, and 8 projections. In some instances, the outer surface 166 has a generally cylindrical profile with a circular cross-section and the projections 168 also have a generally cylindrical profile with a circular cross-section, but with an increased outer diameter relative to the outer surface 166. In that regard, the outer diameter of the projections is between about 0.0127 mm (0.0005") and about 0.0762 mm (0.003") greater than the diameter of the outer surface 166 in some instances, with some particular embodiments being 0.0127 mm (0.0005"), 0.019 mm (0.00075"), and 0.0254 mm (0.001") greater. Accordingly, in some instances the outer surface 166 is recessed with respect to the projections 168 by a distance between about 0.0127 mm (0.0005") and about 0.0762 mm (0.003"), with some particular embodiments being recessed a distance of 0.0127 mm (0.0005"), 0.019 mm (0.00075"), and 0.0254 mm (0.001"). Surface portions 170 transition the insulating portion 156 between the outer surface 166 and the projections 168. In the illustrated embodiment, the surface portions 170 are tapered surfaces that extend at an oblique angle with respect to a longitudinal axis of the connector portion 150 between the outer surface 166 and the projections 168. In other embodiments, surface portions 170 are omitted such that a step is created at the transition between outer surface 166 and projections 168. In that regard, a surface extending between the outer surface 166 and the projections 168 extends perpendicular to the longitudinal axis of the connector portion 150 in some instances.

In the illustrated embodiment, the projections 168 have a length 172 along the longitudinal axis of the connector portion 150. The length 172 is between about 0.0508 mm (0.002") and about 1.27 mm (0.050") in some instances, with some particular embodiments having a length of 0.127 mm (0.005"), 0.254 mm (0.010"), and 0.508 mm (0.020"). Further, the projections 168 are spaced from another by a distance 174 along the longitudinal axis of the connector portion 150. The distance 174 can be any suitable distance and varies in some instances based on the number of projections utilized, lengths of the projections utilized, and/or other factors. In that regard, it is understood that the projections 168 may have equal spacing along the length of the connector portion 150, unequal spacing along the length of the connector portion 150, and/or a combination of equal and unequal spacing along the length of the connector portion.

In some instances, the projections 168 of insulating portion 156 are sized and shaped to prevent bridging between the conductive portions 152 and 154. In particular, the projections 168 are sized and shaped to minimize the impact of conductive liquid (e.g., blood or saline) bridging conductive portions 152 and 154 across insulating portion 156. Accordingly, in some particular embodiments the projections 168 are 0.010" wide such that the surface tension of any liquid in the portion(s) of the outer surface recessed relative to the projections (e.g., the portions defined by outer surface 166) will pull liquid off of the projection(s) 168 to minimize or eliminate any bridging.

The insulating portion 156 is positioned around a tubular member 176. In that regard, in some instances the diameter of an inner lumen of the insulating portion 156 is sized and shaped such that it can be slidingly advanced over the tubular member 176. Accordingly, in some instances, the diameter of the inner lumen of the insulating portion 156 is approximately equal to but slightly larger (e.g., between about 0.0005" and about 0.001" larger) than the outer diameter of the tubular member 176. Further, the tubular member 176 is configured to be positioned around a core wire and one or more conductors. More specifically, the tubular member 176 includes an inner lumen that is sized and shaped to receive the core wire and conductor(s). In the illustrated embodiment of FIG. 9, for sake of clarity the core wire has been omitted. However, a conductor 178 extends within the lumen of the tubular member 176 as shown. A portion 180 of the conductor 178 extends through an opening in a sidewall of the tubular member 176. In that regard, the opening is in communication with the lumen of the tubular member 176. As discussed below with respect to FIGS. 10-12, in some instances the opening is an elongated slot or slit extending along a length of the tubular member.

The portion 180 of the conductor 178 is electrically coupled to the conductive portion 154. As described herein, conductor 178 may extend through an opening of the tubular member 176 and extend longitudinally between tubular member 176 and conductive portion 154 for a distance. After that distance portion 180 may be positioned adjacent to conductive portion 154. For example, portion 180 is positioned on a proximal side of conductive portion 154 and electrically coupled to the conductive portion 154. In embodiments where the conductor 178 includes an insulating layer or sheath around a conductive core, a section of the insulating layer may be removed to expose a section of the conductive core. Any suitable techniques can be utilized to electrically couple the conductor 178 to the conductive portion 154, including soldering, laser welding, and/or other suitable technique. In some instances, the portion 180 of the conductor 178 is wrapped at least partially around the tubular member 176 such that the soldering or other electrically coupling can be performed away from the opening of the tubular member 176. In some instances, the portion 180 is wrapped around the tubular member 176 between about 90 degrees and about 270 degrees. As an example, in some implementations the portion 180 of the conductor 178 is wrapped around the tubular member such that the conductor 178 is soldered or otherwise electrically coupled to the conductive portion 154 opposite to the opening of the tubular member (i.e., approximately 180 degrees around the circumference of the tubular member from the opening). With the portion 180 of conductor 178 wrapped around the tubular member 176, the conductor 178 will be positioned between the conductive portion 154 and the insulating portion 156 such that a gap or spacing 182 is created between the conductive portion 154 and the insulating portion 156. In some instances, the spacing 182 is substantially equal to an outer diameter of the conductor 178. Accordingly, in some implementations the spacing 182 is between about 0.0254 mm (0.001") and about 0.0762 mm (0.003"). However, the spacing 182 is larger in other implementations. It should be noted, that while a single conductor 178 is illustrated in other instances a plurality of conductors may be passed through the opening in the tubular member 176 and electrically coupled to the conductive portion 154.

It is understood that arrangements similar to that shown in FIG. 9 can be repeated for any number of conductive portions of the connector portion 150. In that regard, a single tubular member 176 may extend along the length of the connector portion 150 or a plurality of tubular members may be utilized along the length of the connector portion 150. In that regard, referring now to FIGS. 10-12, shown therein are various embodiments of tubular members according to the present disclosure. The one or more tubular members utilized within the connector portion 150 have a structure similar to the embodiments of FIGS. 10-12 in some instances.

Referring more specifically to FIG. 10, shown therein is a tubular member 190. Tubular member 190 has a body 192 having a generally cylindrical profile with a central lumen extending along its length. The body 192 has a length 194 and a diameter 196. The length 194 varies greatly between implementations and is dependent on various factors such as the number of tubular members utilized for the connector, number of conductive members utilized, size of the conductive members utilized, size of insulating members utilized, and/or other factors. In some instances, the length 194 is between about 12.7 mm (0.5") and about 76.2 mm (3.0"), with some particular embodiments having a length of 41.9 mm (1.65") and 33.0 mm (1.3"). In some implementations, the diameter 196 is between 0.0178 mm (0.0007") and about 0.4572 mm (0.018"). In some instances, the diameter of the inner lumen of the tubular member 190 is between about 0.0127 mm (0.0005") and about 0.4318 mm (0.017"). Accordingly, in some instances the tubular member 190 has a wall thickness between an outer surface of the body 192 and the inner surface defining the lumen between about 0.0127 mm (0.0005") and about 0.254 mm (0.01"), with some particular embodiments having a thickness of 0.0254 mm (0.001"), 0.04064 mm (0.0016"), and 0.0508 mm (0.002").

The tubular member 190 also includes an elongated opening 198 extending along the length of the body 192. In the illustrated embodiment of FIG. 10, the opening 198 extends along the entire length 194 of the body 192. However, in other instances the opening extends along only a portion of the length of the body 192. The opening 198 is in communication with a central lumen 200 of the tubular member 190. In that regard, the opening 198 extends through a sidewall of the body 192 to provide access to the central lumen 200 of the tubular member 190. In the illustrated embodiment, the opening 198 has a substantially constant profile along its length. In particular, the opening 198 has a width 202 that is constant along the length of the opening 198. In some instances, the width 202 of the opening 198 is between about 0.0254 mm (0.001") and about 0.127 mm (0.005"), with some particular embodiments having a width of about 0.0762 mm (0.003"). In other instances, the opening 198 has a variable profile along its length. In that regard, the size, shape, orientation, position around the circumference of the tubular member 190, and/or other aspect of the profile of the opening 198 varies along the length of the opening.

Referring now to FIG. 11, shown therein is a tubular member 210 according to another embodiment of the present disclosure. Tubular member 210 has a body 212 having a generally cylindrical profile with a central lumen extending along its length. The body 212 has a length 214 and a diameter 216. The length 214 varies greatly between implementations and is dependent on various factors such as the number of tubular members utilized for the connector, number of conductive members utilized, size of the conductive members utilized, size of insulating members utilized, and/or other factors. In some instances, the length 214 is between about 12.7 mm (0.5") and about 76.2 mm (3.0"), with some particular embodiments having a length of 41.9 mm (1.65") and 33.0 mm (1.3"). In some instances, the diameter 216 is between 0.0178 mm (0.0007") and about 0.4572 mm (0.018"). In some instances, the diameter of the inner lumen of the tubular member 210 is between about 0.0127 mm (0.0005") and about 0.4318 mm (0.017"). Accordingly, in some instances the tubular member 210 has a wall thickness between an outer surface of the body 212 and the inner surface defining the lumen between about 0.0127 mm (0.0005") and about 0.254 mm (0.01"), with some particular embodiments having a thickness of 0.0254 mm (0.001"), 0.04064 mm (0.0016"), and 0.0508 mm (0.002").

The tubular member 210 also includes an elongated opening 218 extending along the length of the body 212. The opening 218 is in communication with a central lumen 220 of the tubular member 210. In that regard, the opening 218 extends through a sidewall of the body 212 to provide access to the central lumen 220 of the tubular member 210. In the illustrated embodiment of FIG. 11, the opening 218 extends along a majority, but less than the entire length 214 of the body 212. In particular, the opening 218 extends along the body 212 a length 222 that is less than length 214. In some instances, the opening 218 extends along the majority of the length 214 of the body 212 such that only a small section of the body 212 does not include opening 218. For example, in some instances the section of the body that does not include opening 218 extends along the length of the body a distance between about 1.27 mm (0.050") and about 12.7 mm (0.50"), with some particular embodiments having a length of 4.57 mm (0.18"). In the illustrated embodiment, the opening 218 has a substantially constant profile along its length. In particular, the opening 218 has a width 224 that is constant along the length of the opening 218. In some instances, the width 224 of the opening 218 is between about 0.0254 mm (0.001") and about 0.127 mm (0.005"), with some particular embodiments having a width of about 0.0762 mm (0.003"). In other instances, the opening 218 has a variable profile along its length. In that regard, the size, shape, orientation, position around the circumference of the tubular member 210, and/or other aspect of the profile of the opening 218 varies along the length of the opening.

Referring now to FIG. 12, shown therein is a tubular member 230 according to another embodiment of the present disclosure. Tubular member 230 has a body 232 having a generally cylindrical profile with a central lumen extending along its length. The body 232 has a length 234 and a diameter 236. The length 234 varies greatly between implementations and is dependent on various factors such as the number of tubular members utilized for the connector, number of conductive members utilized, size of the conductive members utilized, size of insulating members utilized, and/or other factors. In some instances, the length 234 is between about 12.7 mm (0.5") and about 76.2 mm (3.0"), with some particular embodiments having a length of 41.9 mm (1.65") and 33.0 mm (1.3"). In some instances, the diameter 236 is between 0.0178 mm (0.0007") and about 0.4572 mm (0.018"). In some instances, the diameter of the inner lumen of the tubular member 230 is between about 0.0127 mm (0.0005") and about 0.4318 mm (0.017"). Accordingly, in some instances the tubular member 230 has a wall thickness between an outer surface of the body 232 and the inner surface defining the lumen between about 0.0127 mm (0.0005") and about 0.254 mm (0.01"), with some particular embodiments having a thickness of 0.0254 mm (0.001"), 0.04064 mm (0.0016"), and 0.0508 mm (0.002").

The tubular member 230 also includes an elongated opening 238 extending along the length of the body 232. The opening 238 is in communication with a central lumen 240 of the tubular member 230. In that regard, the opening 238 extends through a sidewall of the body 232 to provide access to the central lumen 240 of the tubular member 230. In the illustrated embodiment of FIG. 12, the opening 238 extends along only a portion of the entire length 234 of the body 232. In particular, the opening 238 extends along the body 232 a length 242 that is less than length 214. In some instances, the length 242 of the opening 238 is between about 30% and about 99% of the total length of the body, with some particular embodiments having a length of about 40%, 50%, 75%, and 90% of the total length of the body. In the illustrated embodiment, the opening 238 has a substantially constant profile along its length. In particular, the opening 238 has a width 244 that is constant along the length of the opening 238. In some instances, the width 244 of the opening 238 is between about 0.0254 mm (0.001") and about 0.127 mm (0.005"), with some particular embodiments having a width of about 0.0762 mm (0.003"). In other instances, the opening 238 has a variable profile along its length. In that regard, the size, shape, orientation, position around the circumference of the tubular member 230, and/or other aspect of the profile of the opening 238 varies along the length of the opening.

The tubular members 190, 210, and 230 of FIGS. 10-12 may be formed of any suitable material. In some embodiments, the tubular member is formed of an insulating material. In some particular embodiments, the tubular member is formed of polyimide.

Referring now to FIGS. 13-19, shown therein are various aspects of assembling a proximal connector portion, such as connector portion 150 illustrated in FIGS. 8 and 9, according to an exemplary embodiment of the present disclosure. Referring initially to FIG. 13, a tubular member 252 is positioned around a core 254 and a plurality of conductors 256, 258, and 260. As shown, the core 254 and the plurality of conductors 256, 258, and 260 extend proximally (to the right as viewed in FIG. 13) beyond the end of the tubular member 252. To facilitate easier illustration of the assembly steps, the core 254 is illustrated in phantom. In that regard, it is understood that in some instances the conductors 256, 258, and 260 are positioned around and run longitudinally along the core 254. In some embodiments, the conductors 256, 258, and 260 are wrapped (e.g., helically, spiral, weaved, or otherwise) around the core 254. In some embodiments, the conductors 256, 258, and 260 extend parallel to the core 254 and parallel to one another. In some embodiments, portions of the conductors 256, 258, and 260 are wrapped (e.g., helically, spiral, weaved, or otherwise) around the core 254, while other portions of the conductors 256, 258, and 260 extend parallel to the core 254. The tubular member 252 is positioned coaxially around the core 254. In other embodiments, the core 254 is offset with respect to a central longitudinal axis of the tubular member 252. In some embodiments, the tubular member 252 is identical or similar to one or more of the embodiments described above with respect to FIGS. 10-12.

Referring now to FIG. 14, connector portion 250 includes an insulating member 260 positioned around the tubular member 252. As shown, the insulating member 260 is positioned coaxially around the tubular member 252. The insulating member 260 may be positioned with a space 251 between it and the tubular member 252. The space 251 may be sized such that a portion of a conductor (such as conductor 256, 258, 260) may extend longitudinally between tubular member 252 and insulating member 260. As discussed herein, the space 251 may be filled with an adhesive or other suitable filling material when insulating member 260 is initially positioned and/or when one or more additional components of connector portion 250 are positioned. In some embodiments, the insulating member 260 is advanced distally along the tubular member 252 until the insulating member 260 is positioned adjacent the distal end of the tubular member 252. In that regard, in some instances the distal end of the tubular member 252 is positioned adjacent to a proximal end of a flexible elongate member (such as flexible elongate member 106), a proximal end of a conductive member, a proximal end of an insulating member, and/or other component positioned of an intravascular device. In one embodiment, the insulating member 260 is advanced along the tubular member until a distal end of the insulating member 260 contacts a proximal end of flexible elongate member 106 of an intravascular device. In some embodiments, insulating member 260 may be omitted.

Referring now to FIG. 15, a conductive element 264 is positioned around the tubular member 252. In some embodiments, the conductive element 264 is advanced distally along the tubular member 252 until the conductive element 264 is positioned adjacent the proximal end of an insulating member 260. The conductive element 264 may be positioned with a space 251 between it and the tubular member 252. The space 251 may be sized such that a portion of a conductor (such as conductor 256, 258, 260) may extend longitudinally between tubular member 252 and conductive element 264. As discussed herein, the space 251 may be filled with an adhesive or other suitable filling material when conductive element 264 is initially positioned and/or when one or more additional components of connector portion 250 are positioned.

In some embodiments, a portion 262a of the conductor 256 is advanced through an opening in the tubular member 252, such as an opening similar to one or more of openings 198, 218, and 238 of tubular members 190, 210, and 238 discussed above. In other embodiments, the tubular member 252 does not include an opening in a sidewall. Instead, the portion 262a extends out of a proximal end of the tubular member and a separate tubular member is then abutted against portion 262a and the proximal end of the tubular member 252. A proximal end or a distal end of a tubular member may be described as an opening. In some instances, the portion 262a is advanced out of tubular member 252 at or near a point half-way along a length 261 of conductive element 264. In other instances, the portion 262a is advanced at a different point along the length 261 of conductive element 264, including points more proximal and more distal than the half-way point. In that regard, the positioning of the opening and/or the size of the tubular member 252 is configured to allow the portion 262a to be advanced radially outward at a desired location relative to the conductive element 264. In some embodiments, the portion 262a of the conductor 256 is wrapped at least partially around the tubular member 252. A portion 262b of the conductor 256 is advanced longitudinally between the conductive element 264 and the tubular member 252 in space 251. In some embodiments, the portion 262b of the conductor 256 is wrapped at least partially around the tubular member 252 as it extends longitudinally. A portion 262c of the conductor 256 is advanced radially outward from space 251 to a position adjacent to conductive element 264. In some embodiments, the portion 262c of the conductor 256 is wrapped at least partially around the tubular member 252. In other embodiments, one or more of portions 262a, 262b, 262c are not wrapped at least partially around the tubular member 252. Rather, for example, portion 262b is advanced longitudinally without wrapping around tubular member 252 and/or the core 254, and extends along the length of the guidewire parallel to tubular member 252. Advancing the portion 262b along the length of the guidewire in space 251 longitudinally separates the connection of the conductor 256 to conductive element 264 from the point at which the conductor 256 passes out of the tubular member 252, thereby making it more difficult for unwanted fluid to reach the core. Accordingly, extending portion 262b along the length of the guidewire advantageously prevents short circuits that may occur if and when a liquid infiltrates connector portion 250 (e.g., adjacent where portion 262c is soldered or otherwise electrically coupled to conductive element 264). This is because the liquid must travel along the distance that the portion 262b extends longitudinally in space 251 to reach the core.

Portion 262c of the conductor 256 is advanced from space 251 to a position adjacent to conductive element 264. According to an exemplary embodiment, portion 262b and/or portion 262c are routed partially under conductive band 264. A slot may be cut into some portion of the conductive band 264 (e.g., underneath, in the side of, etc.). Portion 262c may be received in the slot of the conductive band and soldered therein to the conductive band, which electrically couples conductor 256 and conductive band 264. Thus, portion 262c may be advanced radially outward to a position adjacent to the conductive band 264. In other embodiments, portion 262c may be advanced radially outward to a position adjacent the conductive band 264 without being received in a slot of the conductive band 264 (e.g., to a position between conductive band 264 and insulating member 266 of FIG. 16). The portion 262c of the conductor 256 extending through the opening of the tubular member 252 is electrically coupled to the conductive element 264. Any suitable techniques can be utilized to electrically couple the portion 262c of the conductor 256 to the conductive element 264, including soldering, laser welding, and/or other suitable technique. In some instances, the wrapping of the portion 262c of the conductor 256 around the tubular member 252 and/or removing a portion of an insulating layer or sheath is at least partially performed after the conductive element 264 is positioned around the tubular member 252.

Wrapping the conductor 256 at least partially around the tubular member 252 allows the soldering or other electrically coupling between conductive element 264 and conductor 256 to be performed away from the opening of the tubular member 252. In some instances, one or more of portions 262a, 262b, 262c are wrapped around the tubular member 252 between about 90 degrees and about 270 degrees. In other instances, portions 262a, 262b, and 262c are not wrapped around tubular member 370. As an example, in some implementations the portion 262c of the conductor 256 is wrapped around the tubular member such that the conductor 256 can be soldered or otherwise electrically coupled to a conductive element positioned adjacent to and proximal to the portion 262c on an opposite side of the tubular member 252 from the opening of the tubular member. Further, in embodiments where the conductor 256 includes an insulating layer or sheath around a conductive core, a section of the insulating layer is removed to expose a section of the conductive core. In that regard, it is understood that a section of the portion 262c wrapped around the tubular member 252 includes an insulating layer or sheath in some instances, while the insulating layer or sheath around another section of the portion 262c is removed to expose the underlying conductive material.

Referring now to FIG. 16, an insulating member 266 is positioned around the tubular member 252. As shown, the insulating member 266 is positioned coaxially around the tubular member 252. The insulating member 266 may be positioned with a space 251 between it and the tubular member 252. The space 251 may be sized such that a portion of a conductor (such as conductor 256, 258, 260) may extend longitudinally between tubular member 252 and insulating member 266. As discussed herein, the space 251 may be filled with an adhesive or other filling material when insulating member 266 is initially positioned and/or when one or more additional components of connector portion 250 are positioned. The insulating member 266 is advanced distally along the tubular member 252 until the insulating member 266 is positioned adjacent a proximal end of the conductive element 264. In some instances, the insulating member 266 is advanced distally along the tubular member 252 until a distal end of the insulating member 266 contacts a proximal end of the conductive element 264. In that regard, in some instances the insulating member 266 is advanced until it contacts the portion 262c of the conductor 256 such that the insulating member 266 is spaced from the conductive element 264 by portion 262c.

Referring now to FIG. 17, a conductive element 267 is positioned around the tubular member 252. In some embodiments, the conductive element 267 is advanced distally along the tubular member 252 until the conductive element 267 is positioned adjacent the proximal end of an insulating member 262. The conductive element 267 may be positioned with a space 251 between it and the tubular member 252. The space 251 may be sized such that a portion of a conductor (such as conductor 256, 258, 260) may extend longitudinally between tubular member 252 and conductive element 267. As discussed herein, the space 251 may be filled with an adhesive or other suitable filling material when conductive element 267 is initially positioned and/or when one or more additional components of connector portion 250 are positioned.

Referring now to FIG. 18, a portion 268a of the conductor 258 is advanced through the opening in the tubular member 252. In other embodiments, the tubular member 252 does not include an opening in the sidewall. Instead, the portion 268a extends out of a proximal end of the tubular member 252 and a separate tubular member is then abutted against portion 262a and the proximal end of the tubular member 252. A proximal end or a distal end of a tubular member may be described as an opening. In some instances, the portion 268a is advanced out of tubular member 252 at or near a point half-way along a length 265 of conductive element 267. In other instances, the portion 268a is advanced at a different point along the length 265, including points more proximal and more distal than the half-way point. In that regard, the positioning of the opening and/or the size of the tubular member 252 is configured to allow the portion 268a to be advanced radially outward at a desired location relative to the conductive element 267. In some embodiments, the portion 268a of the conductor 258 is wrapped at least partially around the tubular member 252. A portion 268b of the conductor 256 is advanced longitudinally between the conductive element 265 and the tubular member 252 in space 251. In some embodiments, the portion 268b of the conductor 258 is wrapped at least partially around the tubular member 252. A portion 268c of the conductor 258 is advanced from space 251 to a position adjacent to conductive element 267. In some embodiments, the portion 268c of the conductor 256 is wrapped at least partially around the tubular member 252. In other embodiments, one or more of portions 268a, 268b, 268c are not wrapped at least partially around the tubular member 252. Rather, for example, portion 268b is advanced longitudinally without wrapping around tubular member 252 and/or the core 254, and extends along the length of the guidewire parallel to tubular member 252. Advancing the portion 268b along the length of the guidewire in space 251 longitudinally separates the connection of the conductor 258 to conductive element 267 from the point at which the conductor 258 passes out of the tubular member 252, thereby making it more difficult for unwanted fluid to reach the core. Accordingly, extending portion 268b along the length of the guidewire advantageously prevents short circuits that may occur if and when a liquid infiltrates connector portion 250 (e.g., adjacent where portion 268c is soldered or otherwise electrically coupled to conductive element 267). This is because the liquid must travel along the distance that the portion 268b extends longitudinally in space 251 to reach the core.

Portion 268c of the conductor 258 is advanced from space 251 to a position adjacent to conductive element 267. According to an exemplary embodiment, portion 268b and/or portion 268c are routed partially under conductive band 267. A slot may be cut into some portion of the conductive band 267 (e.g., underneath, in the side of, etc.). Portion 268c may be received in the slot of the conductive band and soldered therein to the conductive band, which electrically couples conductor 258 and conductive band 267. Thus, portion 268c may be advanced radially outward to a position adjacent to the conductive band 267. In other embodiments, portion 268c may be advanced to a position adjacent the conductive band 267 without being received in a slot of the conductive band 267 (e.g., to a position between conductive band 267 and insulating member 270 of FIG. 19). The portion 268c of the conductor 258 extending through the opening of the tubular member 252 is electrically coupled to the conductive element 267. Any suitable techniques can be utilized to electrically couple the portion 268c of the conductor 258 to the conductive element 267, including soldering, laser welding, and/or other suitable technique. In some instances, the wrapping of the portion 268c of the conductor 258 around the tubular member 252 and/or removing a portion of an insulating layer or sheath is at least partially performed after the conductive element 267 is positioned around the tubular member 252.

Wrapping the conductor 258 at least partially around the tubular member 252 allows the soldering or other electrically coupling can be performed away from the opening of the tubular member 252. In some instances, one or more of portions 268a, 268b, 268c are wrapped around the tubular member 252 between about 90 degrees and about 270 degrees. In other instances, portions 268a, 268b, and 268c are not wrapped around tubular member 370. As an example, in some implementations the portion 268c of the conductor 258 is wrapped around the tubular member such that the conductor 258 can be soldered or otherwise electrically coupled to a conductive element positioned adjacent to and proximal to the portion 268c on an opposite of the tubular member 252 from the opening of the tubular member. Further, in embodiments where the conductor 258 includes an insulating layer or sheath around a conductive core, a section of the insulating layer is removed to expose a section of the conductive core. In that regard, it is understood that a section of the portion 268c wrapped around the tubular member 252 includes an insulating layer or sheath in some instances, while the insulating layer or sheath around another section of the portion 268c is removed to expose the underlying conductive material.

Referring now to FIG. 19, an insulating member 270 is positioned around the tubular member 252. As shown, the insulating member 270 is positioned coaxially around the tubular member 252. The insulating member 270 may be positioned with a space 251 between it and the tubular member 252. The space 251 may be sized such that a portion of a conductor (such as conductor 256, 258, 260) may extend longitudinally between tubular member 252 and insulating member 270. As discussed herein, the space 251 may be filled with an adhesive or other suitable filling material when insulating member 270 is initially positioned and/or when one or more additional components of connector portion 250 are positioned. The insulating member 270 is advanced distally along the tubular member 252 until the insulating member 270 is positioned adjacent a proximal end of the conductive element 267. In some instances, the insulating member 270 is advanced distally along the tubular member 252 until a distal end of the insulating member 270 contacts a proximal end of the conductive element 267. In that regard, in some instances the insulating member 270 is advanced until it contacts the portion 268c of the conductor 258 such that the insulating member 270 is spaced from the conductive element 267 by portion 268c.

Steps similar to those described in FIGS. 14-19 can be repeated to electrically couple additional conductive elements to the plurality of conductors extending along the core wire for any number of conductors and/or conductive elements. Further, in some embodiments, multiple conductors of the plurality of conductors are coupled to a single conductive element. For example, in one embodiment two conductors are coupled to a single conductive element. In one such embodiment, the two conductors are electrically coupled to the conductive element adjacent to one another. In other embodiments, the two conductors are electrically coupled to the conductive element and spaced apart from one another. For example, one of the conductors is electrically coupled to a distal end of the conductive element, while the other conductor is electrically coupled to a proximal end of the conductive element. In one particular implementation, one of the conductors is wrapped around the tubular member 252 adjacent a distal end of the conductive element, while the other conductor is wrapped around the tubular member adjacent to a proximal end of the conductive element.

In some instances, an adhesive is utilized to secure one or more of the components in place. For example, in some instances, either during each component placement or after all components are placed and soldered together, the components are secured together with an adhesive or other suitable material. In that regard, securing the components together serves to greatly reduce or eliminate potential problems with the resulting device. For example, in some implementations securing the components together prevents relative rotation of the components that can lead to conductor breakage. As another example, the adhesive can also fill any potential fluid paths that lead to internal bridging. Accordingly, in some instances, all internal gaps between a conductive bands/insulating spacers and the insulating tubular member or support structure below is filled with adhesive. Such an approach serves to eliminate any internal fluid pathways that may create a bridging effect and ensures that all components are fixedly secured to one another such that they won't mechanically shift, slip, and/or rotate relative to other components. Further, in some instances adhesive is also positioned between adjacent conductive bands and insulating spacers. In some embodiments, similar implementations of adhesives are used for the other embodiments of the present disclosure described below.

Generally, the adhesive(s) can be any adhesive that provides adequate locking of the components and/or gap filling capability to eliminate internal fluid bridging. In some instances the adhesive is a UV cured adhesive. Further, in some instances, the adhesive also includes a heat cure and/or a secondary moisture cure to facilitate curing of areas that can't be UV cured. A flexible adhesive is used in some instances. One or more of the following adhesive characteristics is taken into consideration in selecting the adhesive: adhesion and shear strength (e.g., to ensure that the component(s) can't rotate or slip, which would likely result in a broken electrical connection and could allow fluid bridging); water resistance (e.g., water resistance adequate to eliminate potential for internal bridging of the electrical contacts); viscosity (e.g., viscosity low enough to allow the adhesive to fill in the relatively small spaces that would allow for fluid migration. It should be noted, however, that adhesives that are slightly too viscous to wick into the gaps naturally can be forced into the assembly gaps using pressurized application methods.); flexibility (e.g., to allow for the typical manipulation of the proximal portion of the intravascular device during use. In particular, if adhesive positioned under the insulating members cracks or otherwise separates due to bending or other manipulation, internal fluid paths may open up between the conductive bands); and/or other suitable adhesive characteristics. Examples of the types of adhesives that can be used include: UV cured with secondary heat cure (e.g., Dymax adhesives); UV cured, low viscosity silicones with secondary moisture cure (this type is preferable in some applications because of the flexibility and water resistance); cyanoacrylates; and/or other known or future developed adhesives.

Figure 21:
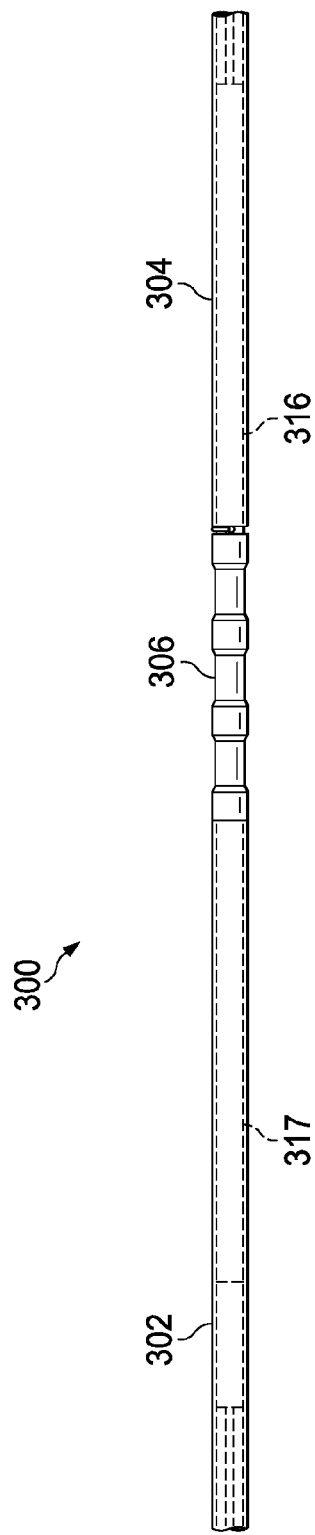
FIG. 21 is a diagrammatic side view of a portion of the proximal connector portion of FIG. 20 with inner components of the proximal connector portion illustrated.
Figure 22:
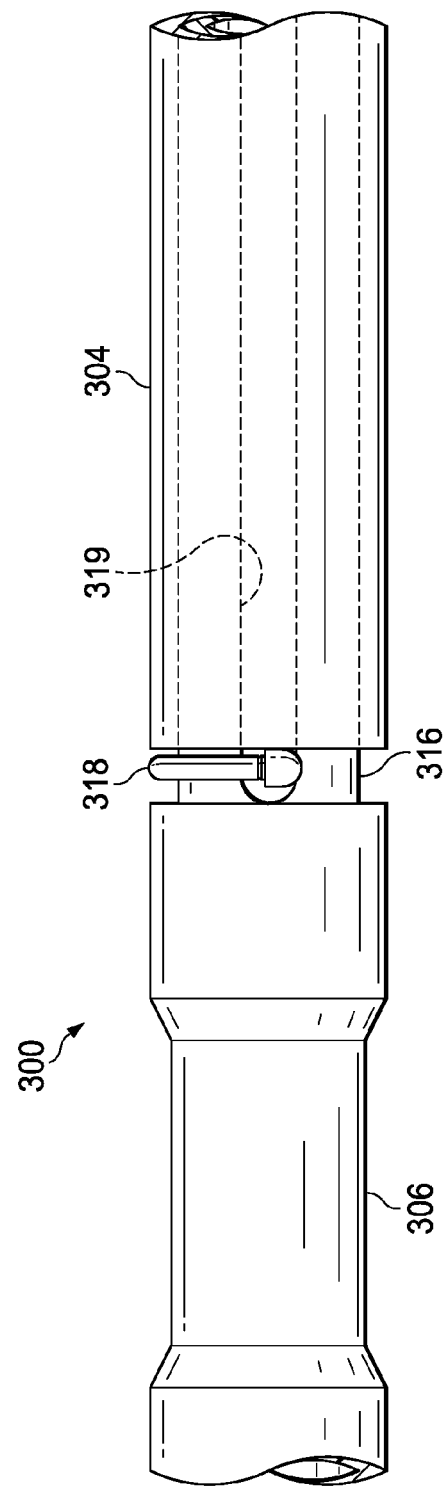
FIG. 22 is a close-up diagrammatic side view of a portion of the proximal connector portion of FIGS. 20 and 21 with inner components of the proximal connector portion illustrated.

Referring now to FIGS. 20-22, shown therein are aspects of a connector portion 300 of an intravascular device according to an embodiment of the present disclosure. As shown in FIG. 20, the connector portion 300 includes conductive portions 302, 304 and insulating portions 306, 308. In that regard, the insulating portion 306 separates the conductive portion 302 from the conductive portion 304. In some instances, the insulating portion 308 separates the conductive portion 302 from one or more other conductive portions (not shown) of the connector portion 300. A section 310 extending proximally from the connector portion 300 to another section 312 that extends to a proximal end 314. The sections 310, 312 have structures and arrangements as described above with respect to sections 118, 120 and 160, 162 in some instances. As discussed below, in some instances the connector portion 300 includes an element that defines structures similar to those of tubular member 252 and one or more of the insulating members 160, 166 in a single, integrally formed member. In that regard, a plurality of such elements are utilized in some implementations to electrically couple a plurality of conductive elements to a plurality of conductors as described below in the context of FIGS. 29-34.

Referring now to FIGS. 21 and 22, shown therein are additional details of the proximal connector portion 300. As shown, the insulating portion 306 includes an outer surface having a plurality of projections similar to insulating portion 156 described above. In that regard, the connector portion 300 can include any number of projections (or omit the projections entirely), but in some embodiments the connector portion 300 includes between 1 and 20 projections, with some particular embodiments having 0, 1, 5, and 8. In some instances, the connector portion 300 has a generally cylindrical profile with a circular cross-section and the projections likewise have a generally cylindrical profile with a circular cross-section, but with an increased outer diameter relative to the outer surface. In that regard, the outer diameter of the projections is between about 0.0127 mm (0.0005") and about 0.0762 mm (0.003") greater than the diameter of the outer surface of the connector portion 300 in some instances, with some particular embodiments being 0.0127 mm (0.0005"), 0.019 mm (0.00075"), and 0.0254 mm (0.001") greater. Accordingly, in some instances the outer surface of the connector portion 300 is recessed with respect to the projections by a distance between about 0.0127 mm (0.0005") and about 0.0762 mm (0.003"), with some particular embodiments being recessed a distance of 0.0127 mm (0.0005"), 0.019 mm (0.00075"), and 0.0254 mm (0.001"). The projections have a length along the longitudinal axis of the connector portion 300 about 0.0508 mm (0.002") and about 1.27 mm (0.050") in some instances, with some particular embodiments having a length of 0.127 mm (0.005"), 0.254 mm (0.010"), and 0.508 mm (0.020"). Further, the projections are spaced from another by a distance along the longitudinal axis of the connector portion 300. The spacing distance can be any suitable distance and varies in some instances based on the number of projections utilized, lengths of the projections utilized, and/or other factors. In that regard, it is understood that the projections may have equal spacing along the length of the connector portion 300, unequal spacing along the length of the connector portion 300, and/or a combination of equal and unequal spacing along the length of the connector portion 300.

In some embodiments, the connector portion 300 includes transitions between the outer surface and the projections. In the illustrated embodiment, the transitions are tapered surfaces that extend at an oblique angle with respect to a longitudinal axis of the connector portion 300. In other embodiments, the transitions are omitted such that a step is created at the transition between outer surface and one or more of the projections. In that regard, a surface extending between the outer surface and the projection outer surface extends perpendicular to the longitudinal axis of the connector portion 300 in some instances.

As best seen in FIG. 21, the insulating portion 306 is integrally formed with tubular portions 316 and 317. In that regard, in some instances the tubular portions 316 and 317 include structures and/or features similar to those described above with respect to tubular members 176, 190, 210, 230, and 252. In that regard, the tubular portions 316 and 317 are configured to be positioned around a core wire and one or more conductors in some instances. More specifically, in some embodiments the tubular portions 316 and 317 include an inner lumen that is sized and shaped to receive the core wire and conductor(s). In that regard, the inner lumen extends continuously through the insulating portion 306 positioned between the tubular portions 316 and 317 in some embodiments. As shown, the tubular portion 316 is configured to be positioned within a distal section of conductive portion 304, while tubular portion 317 is configured to be positioned within a proximal section of conductive portion 302. As shown in FIG. 22, a conductor 318 extends within the lumen of the tubular portion 317, the insulating portion 306, and the tubular portion 316 and extends through an opening 319 in a sidewall of the tubular portion 316. In that regard, the opening 319 is in communication with the lumen. The opening 319 is an elongated slot or slit extending along a length of the tubular portion 316 in some instances.

The conductor 318 is electrically coupled to the conductive portion 304. As described herein, conductor 318 may extend through an opening 319 of the tubular member 316 and extend longitudinally between tubular member 316 and conductive portion 304 for a distance. After that distance conductor 318 may be positioned adjacent to conductive portion 304. For example, conductor 318 is positioned on a proximal side of conductive portion 304 and electrically coupled to the conductive portion 304. In embodiments where the conductor 318 includes an insulating layer or sheath around a conductive core, a section of the insulating layer may be removed to expose a section of the conductive core. Any suitable techniques can be utilized to electrically couple the conductor 318 to the conductive portion 304, including soldering, laser welding, and/or other suitable technique. In some instances, the conductor 318 is wrapped at least partially around the tubular portion 316 such that the soldering or other electrically coupling can be performed away from the opening 319 of the tubular portion 316. In some instances, the conductor 318 is wrapped around the tubular portion 316 between about 90 degrees and about 270 degrees. As an example, in some implementations the conductor 318 is wrapped around the tubular portion 316 such that the conductor 318 is soldered or otherwise electrically coupled to the conductive portion 304 opposite to the opening 319 of the tubular portion 316 (i.e., approximately 180 degrees around the circumference of the tubular member from the opening). With the conductor 318 wrapped around the tubular portion 316, the conductor 318 will be positioned between the conductive portion 304 and the insulating portion 306 such that a gap or spacing is created between the conductive portion 304 and the insulating portion 306. In some instances, the spacing is substantially equal to an outer diameter of the conductor 318. Accordingly, in some implementations the spacing is between about 0.0254 mm (0.001") and about 0.0762 mm (0.003"). However, the spacing is larger in other implementations. It should be noted, that while a single conductor 318 is illustrated in other instances a plurality of conductors may be passed through the opening 319 in the tubular portion 316 and electrically coupled to the conductive portion 304.

It is understood that arrangements similar to that shown in FIGS. 21 and 22 can be repeated for any number of conductive portions of the connector portion 300. In that regard, in some instances a kit consisting of a plurality of insulating portions and a plurality of conductive portions is provided. A user can then assemble a connector portion having a desired number of electrically isolated conductive portions by positioning an insulating portion between a pair of conductive portions. In some instances, the provided insulating portions of the kit all have the same structure. In other instances, the kit includes insulating portions with varying structures/features. In particular, in some instances the insulating portions has (a) a pair of tubular portions integrally formed therewith (e.g., similar to the arrangement of insulating portion 306 and tubular portions 316 and 317 of FIGS. 21 and 22), (b) a single tubular portion integrally formed therewith (e.g., an arrangement of insulating portion 306 that would include only one of the tubular portions 316 and 317, see also FIG. 28), or (c) no tubular portion integrally formed therewith (e.g., an arrangement of insulating portion 306 that does not include either of the tubular portions 316 and 317). In that regard, in some instances an insulating portion with a single tubular portion integrally formed therewith is particularly suitable for use in isolating a distal most conductive portion of the connector portion 300 from the flexible elongate member 106 of the intravascular device 102.

Figure 23:
FIG. 23 is a diagrammatic side view of an element for forming a component of the proximal connector portion of FIGS. 20-22 according to an embodiment of the present disclosure.
Figure 24:
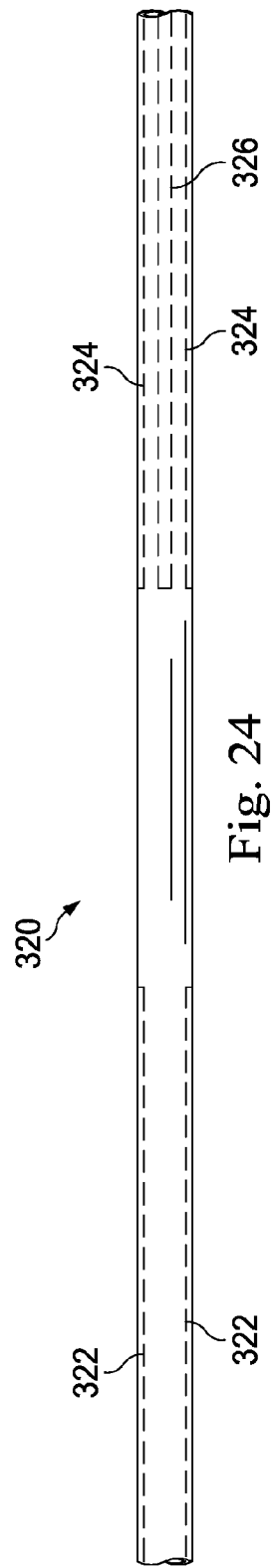
FIG. 24 is a diagrammatic side view of the element of FIG. 23 with markings showing portions of the element that will be removed to form a component of the proximal connector portion of FIGS. 20-22 according to an embodiment of the present disclosure.
Figure 25:
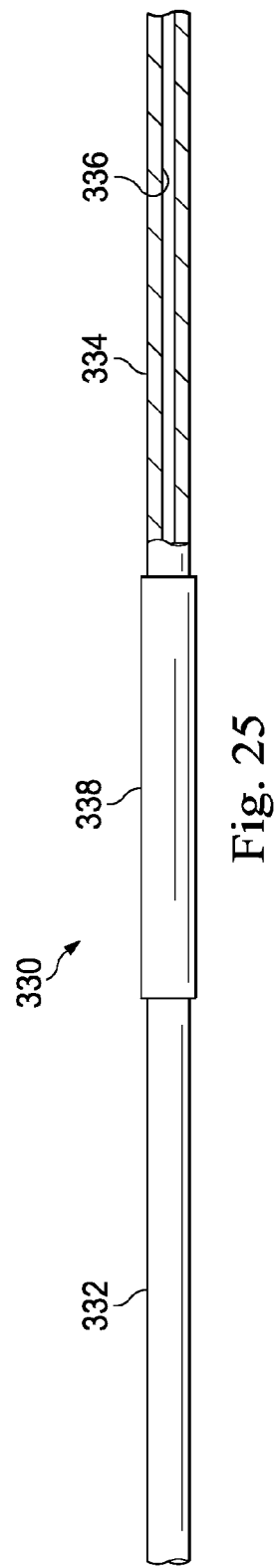
FIG. 25 is a diagrammatic side view of a component of the proximal connector portion of FIGS. 20-22 formed from the element of FIG. 23 according to the markings shown in FIG. 24.

Referring now to FIGS. 23-25, shown therein are various stages of the formation of an insulating member according to an embodiment of the present disclosure. In that regard, FIG. 23 shows a tubular member 320. In some instances, tubular member 320 has a cylindrical outer profile with an outer diameter between about 0.0178 mm (0.0007") and about 3.0 mm (0.118"), with some particular embodiments having an outer diameter of 0.3556 mm (0.014"), 0.3683 mm (0.0145") and 0.4572 (0.018"). Further, in some embodiments, the tubular member 320 has an inner lumen extending along its length. In some instances, the inner lumen has a circular cross-sectional profile with a diameter less than the outer diameter. In that regard, the diameter of the lumen is between about 0.0508 mm (0.002") and about 0.254 mm (0.01") less than the outer diameter of the tubular member 320 in some instances, with some particular embodiments being between about 0.1016 mm (0.004") and 0.127 mm (0.005") less. Generally, the tubular member 320 can have any length as the tubular member 320 may be cut, ablated, and/or otherwise reduced in length or separated into multiple pieces based on a desired length for the particular insulating member being formed in accordance with the present disclosure. In some implementations, the desired length of the insulating member is between about 12.7 mm (0.5") and about 76.2 mm (3.0"), with some particular embodiments having a length of 41.9 mm (1.65") and 33.0 mm (1.3"). In that regard, in FIGS. 23-25 the tubular member 320 is illustrated as having already been processed to the desired length. The tubular member 320 is formed of an insulating material in some embodiments. For example, in some particular embodiments the tubular member 320 is formed of polyimide.

Referring more specifically to FIG. 24, portions of the tubular member 320 that are to be removed to create the desired structure of the insulating member are identified. In that regard, dashed lines 322 and 324 illustrate portions of the tubular member that will be removed completely. In the illustrated embodiment, the dashed lines 322 and 324 are indicative of a circumferential removal of material about the outer diameter of the tubular member 320. Accordingly, as shown, removal of the material indicated by lines 322 and 324 serves to provide the tubular member with outer portions having a reduced diameter with respect to a central portion, where material is not removed. In that regard, in some instances the lines 322 and 324 are positioned inside the outer diameter of the tubular member 320, such that the resulting tubular portions with reduced diameters have outer diameters that are between 0.0254 mm (0.001") and about 0.1 mm (0.01") less than the outer diameter of the tubular member 320, with some particular embodiments being between about 0.0508 mm (0.002") and 0.127 mm (0.005") less. Dashed lines 326 represent a portion of the tubular member 320 where material will be removed through one sidewall of the tubular member 320. In other words, material will be removed from the outer surface until the inner lumen of the tubular member is accessed for the area represented by dashed lines 326. The portion of the sidewall of the tubular member 320 opposite lines 326 is not removed in the illustrated embodiment. However, in other instances, a portion, portions, or all of the sidewall of the tubular member 320 opposite lines 326 is removed. In that regard, in some embodiments, opposed openings are created within the opposing sidewalls of the tubular member 320 along the path defined by lines 326. The material of tubular member 320 to be removed, as indicated by lines 322, 324, and 326, can be removed using any suitable technique for the particular material. Accordingly, in some instances the material is laser ablated.

Referring now to FIG. 25, shown therein is an insulating member 330 formed by removing the material along lines 322, 324, and 326 as described above. As shown, the insulating member 330 includes a tubular portion 332 (defined by the removal of material along lines 322), a tubular portion 334 that includes an opening 336 extending along its length (defined by the removal of material along lines 324 and 326), and an insulating portion 338 positioned between tubular portions 332 and 334. In that regard, the insulating portion 338 has the same outer diameter as tubular member 320 in some instances. In other instances, an outer portion of the tubular member 320 is also removed to define insulating portion 338 as well.

Referring now to FIGS. 23, 26, and 27, shown therein are various stages of the formation of an insulating member according to another embodiment of the present disclosure. Again, FIG. 23 shows tubular member 320 that is utilized to form the insulating member. Referring more specifically to FIG. 26, portions of the tubular member 320 that are to be removed to create the desired structure of the insulating member are identified. In that regard, dashed lines 342, 344, and 346 are substantially similar to lines 322, 324, and 326, respectively, described above. Accordingly, these portions will not be discussed in detail again. However, the plurality of dashed lines 348 illustrate portions of the tubular member that will be removed to define projections of an insulating portion of the insulating member. In that regard, the dashed lines 348 of the illustrated embodiment generally have a profile configured to define a plurality of projections having structures similar to those of projections 168 illustrated in FIG. 9. However, it is understood that the dashed lines 348 can be configured to define any desired projection shape and/or transition type between the projection and other portions of the insulating member. In the illustrated embodiment, the dashed lines 348 are indicative of a circumferential removal of material about the outer diameter of the tubular member 320.

Accordingly, as shown in FIG. 27, removal of the material indicated by lines 348 serves to provide the tubular member 350 with outer portions 351 having a reduced diameter with respect to the resulting projections 352 where material is not removed (or removed to a lesser extent). In that regard, in some instances the lines 348 have a depth such that the resulting portions 351 with reduced diameters have outer diameters that are between 0.0127 mm (0.0005") and about 0.0762 mm (0.003") less than the outer diameter of the projections 352, with some particular embodiments being 0.0127 mm (0.0005"), 0.019 mm (0.00075"), and 0.0254 mm (0.001") less. In that regard, the insulating member 350 formed by removing the material along lines 342, 344, 346, and 348 as described above includes a tubular portion 353 (defined by the removal of material along lines 342), a tubular portion 354 that includes an opening 356 extending along its length (defined by the removal of material along lines 344 and 346), and an insulating portion 358 positioned between tubular portions 353 and 354 (defined by the removal of material along lines 348). In that regard, the projections 352 of insulating portion 358 have the same outer diameter as tubular member 320 in some instances. In other instances, an outer portion of the tubular member 320 is also removed to define projections 352 of insulating portion 358 as well.

Referring now to FIG. 28, shown therein is an insulating member 360 according to another embodiment of the present disclosure. As shown, the insulating member 360 includes an insulating portion 362 and a tubular portion 364. The tubular portion 364 has a reduced profile relative to the insulating portion 362 and includes an opening 366 extending along its length. In some instances, the insulating portion 362 and the tubular portion 364 are similar to insulating portions and tubular portions, respectively, of other embodiments of the present disclosure. However, as shown, the insulating member 360 includes only one tubular portion such that the insulating portion 362 defines one end of the insulating member 360 and the tubular portion 364 defines the opposing end of the insulating member. In some implementations, insulating members having structures similar to insulating member 360 are utilized for the distal most and/or proximal most insulating members of a connector portion of an intravascular device.

Referring now to FIGS. 29-34, shown therein are various aspects of assembling a proximal connector portion, such as connector portion 300 illustrated in FIGS. 20-22, according to an exemplary embodiment of the present disclosure. Referring initially to FIG. 29, an insulating member 370 is positioned around a core 254 and a plurality of conductors 256, 258, and 260. As shown, the core 254 and the plurality of conductors 256, 258, and 260 extend proximally (to the right as viewed in FIGS. 29-33) beyond the end of the insulating member 370. In some embodiments, insulating portion 362 and insulating member are integrally formed such that they are a contiguous element. In other embodiments, insulating portion 362 and insulating member 370 are separate elements, and insulating portion 362 is positioned coaxially around insulating members 370. Again, to facilitate easier illustration of the assembly steps, the core 254 is illustrated in phantom. In that regard, it is understood that in some instances the conductors 256, 258, and 260 are positioned around and run longitudinally along the core 254. In some embodiments, the conductors 256, 258, and 260 are wrapped (e.g., helically, spiral, weaved, or otherwise)

around the core 254. In some embodiments, the conductors 256, 258, and 260 extend parallel to the core 254 and parallel to one another without wrapping around the core and extending along the length of the guidewire. In some embodiments, portions of the conductors 256, 258, and 260 are wrapped (e.g., helically, spiral, weaved, or otherwise) around the core 254, while other portions of the conductors 256, 258, and 260 extend parallel to the core 254 without rotating around the core. The insulating member 370 is positioned coaxially around the core 254. In other embodiments, the core 254 is offset with respect to a central longitudinal axis of the insulating member 370. In some embodiments, the insulating member 370 is identical or similar to one or more of the embodiments described above with respect to FIG. 21, 22, 25, 27, or 28. In the illustrated embodiment, insulating member 370 is similar to insulating member 360 of FIG. 28.

Referring now to FIG. 30, a conductive element 374 is positioned around the tubular member 370. In some embodiments, the conductive element 374 is advanced distally along the tubular member 370 until the conductive element 374 is positioned adjacent the proximal end of an insulating portion 362. In one embodiment, tubular member 370 is positioned relative to the conductive element 374 such that at least one end (e.g., the proximal end in FIG. 30) of the tubular member 370 is at or near a point half-way along a length of conductive element 374. In other embodiments, at least one end of the tubular member 370 is at a different point along the length of conductive element 374, including points more proximal and more distal than the half-way point. The conductive element 374 may be positioned with a space 371 between it and the tubular member 370. The space 371 may be sized such that a portion of a conductor (such as conductor 256, 258, 260) may extend longitudinally between tubular member 370 and conductive element 374. As discussed herein, the space 371 may be filled with an adhesive or other suitable filling material when conductive element 374 is initially positioned and/or when one or more additional components of insulating member 360 are positioned.

A portion 372a of the conductor 256 is advanced through an opening in the tubular member 370. The opening may be similar to one or more of openings 319, 336, 356, and 366 discussed above. In other embodiments, the tubular member 370 does not include an opening in the sidewall. Instead, the portion 372a extends out of a proximal end of the tubular member 370 and a separate tubular member is then abutted against portion 372a and the proximal end of the tubular member 370. A proximal end or a distal end of a tubular member may be described as an opening. In such embodiments, tubular member 370 may not have an opening or slot in the wall thereof to allow portion 372(a) to advance through and out of the tubular members 370. Instead, portion 372(a) may advance via a space 378 (FIG. 31) between adjacent tubular members (e.g., tubular members 370, 375 of FIG. 31). In some instances, the portion 372a is advanced out of tubular member 370 at or near a point half-way along a length 388 of conductive element 374. In other instances, the portion 372a is advanced at a different point along the length 388 of conductive element 374, including points more proximal and more distal than the half-way point. In that regard, the positioning of the opening and/or the size of the tubular member 370 is configured to allow the portion 372a to be advanced radially outward at a desired location relative to the conductive element 374. In some embodiments, the portion 372a of the conductor 256 is wrapped at least partially around the tubular member 370. A portion 372b of the conductor 256 is advanced longitudinally between the conductive element 374 and the tubular member 370 in space 371. In some embodiments, the portion 372b of the conductor 256 is wrapped at least partially around the tubular member 370. In other embodiments, the portion 372(b) extends along the length of core 254 in space 371 without wrapping around tubular member 370 and/or core 254. A portion 372c of the conductor 256 is advanced from space 371 to a position adjacent to conductive element 374. In some embodiments, the portion 372c of the conductor 256 is wrapped at least partially around the tubular member 370. Advancing the portion 372b longitudinally in space 371 advantageously prevents short circuits that may occur if and when a conductive liquid infiltrates insulating member 360 (e.g., at a point where portion 372c is soldered or otherwise electrically coupled to conductive element 374). This is because a conductive liquid must travel along the distance that the portion 372b extends longitudinally in space 371 to reach the core.

The portion 372c of the conductor 256 is electrically coupled to the conductive element 374. According to an exemplary embodiment, portion 372b and/or portion 372c are routed partially under conductive band 374. A slot may be cut into some portion of the conductive band 374 (e.g., underneath, in the side of, etc.). Portion 372c may be received in the slot of the conductive band and soldered therein to the conductive band, which electrically couples conductor 256 and conductive band 374. Thus, portion 372c may be advanced radially outward to a position adjacent to the conductive band 374. In other embodiments, portion 372c may be advanced to a position adjacent the conductive band 374 without being received in a slot of the conductive band 374 (e.g., to a position between conductive band 374 and insulating member 376 of FIG. 31). Any suitable techniques can be utilized to electrically couple the portion 372c of the conductor 256 to the conductive element 374, including soldering, laser welding, and/or other suitable technique. In some instances, the wrapping of the portion 372c of the conductor 256 around the tubular member 370 and/or removing a portion of an insulating layer or sheath is at least partially performed after the conductive element 374 is positioned around the tubular member 370.

Wrapping the conductor 256 at least partially around the tubular member 370 allows the soldering or other electrically coupling can be performed away from the opening of the tubular member 370. In some instances, one or more of portions 372a, 372b, 372c are wrapped around the tubular member 370 between about 90 degrees and about 270 degrees. In other instances, portions 372a, 372b, and 372c are not wrapped around tubular member 370. As an example, in some implementations the portion 372c of the conductor 256 is wrapped around the tubular member such that the conductor 256 can be soldered or otherwise electrically coupled to a conductive element positioned adjacent to and proximal to the portion 372c on an opposite of the tubular member 370 from the opening of the tubular member. Further, in embodiments where the conductor 256 includes an insulating layer or sheath around a conductive core, a section of the insulating layer is removed to expose a section of the conductive core. In that regard, it is understood that a section of the portion 372c wrapped around the tubular member 370 includes an insulating layer or sheath in some instances, while the insulating layer or sheath around another section of the portion 372c is removed to expose the underlying conductive material.

Figure 31:
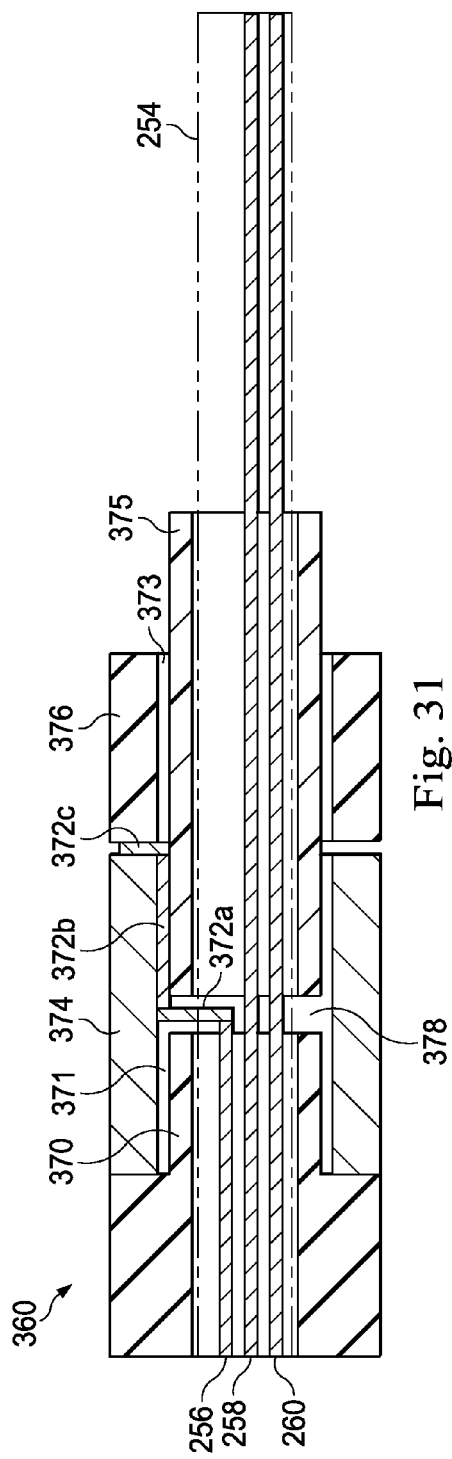

Referring now to FIG. 31, an insulating member 376 and tubular member 375 are positioned around a core 254 and conductors 258 and 260. The insulating member 376 and tubular member 375 ares positioned coaxially around the core 254. In some embodiments, insulating member 376 and tubular member 375 are separate elements. For example, tubular member 375 may be positioned around core 254 and conductors 258 and 260 first and thereafter, insulating member 376 maybe position around tubular member 375. The insulating member 376 may be positioned with a space 373 between it and the tubular member 375. The space 373 may be sized such that a portion of a conductor (such as conductor 256, 258, 260) may extend longitudinally between tubular member 375 and insulating member 376. As discussed herein, the space 373 may be filled with an adhesive or other suitable filling material when insulating member 376 is initially positioned and/or when one or more additional components of insulating member 360 are positioned. In other embodiments, insulating member 376 and tubular member 375 are integrally formed and are not separate elements. In such embodiments, no space may be disposed between insulating member 376 and tubular member 375. However, a space may still be disposed between tubular member 375 and adjacent conductive elements 374, 382 (e.g., space 371 and space 373, respectively).

In other embodiments, the core 254 is offset with respect to a central longitudinal axis of the insulating member 376. In some embodiments, the insulating member 376 is identical or similar to one or more of the embodiments described above with respect to FIG. 21, 22, 25, 27, or 28. In the illustrated embodiment, insulating member 376 is similar to insulating member 330 of FIG. 25. The insulating member 376 is advanced distally over the core 254 until an insulating portion of the insulating member 376 is positioned adjacent to a proximal end of the conductive element 374. In some instances, the insulating member 376 is advanced distally along the core 254 until a distal end of the insulating portion of the insulating member 376 contacts a proximal end of the conductive element 374. In that regard, in some instances the insulating member 376 is advanced until it contacts the portion 372c of the conductor 256 such that the insulating member 376 is spaced from the conductive element 374 by portion 372c.

In the illustrated embodiment, a distal portion of the tubular member 375 extends within conductive element 374. As shown, the distal end of the distal portion of the tubular member 375 is spaced from the proximal end of the proximal portion of tubular member 370, represented by space 378. Generally, the length of space 378 along the longitudinal axis of the core 254 is between about 0.127 mm (0.005") and about 5.08 mm (0.20"), with some particular embodiments having lengths of 1.27 mm (0.050"), 2.54 mm (0.10"), and 3.81 mm (0.150"). In that regard, the length of space 378 is representative of the distance between the distal end of the distal portion of the tubular member 375 and the proximal end of the proximal portion of tubular member 370. In some instances, there is no space between the distal end of the distal portion of the tubular member 375 and the proximal end of the proximal portion of tubular member 370. In other words, the tubular member 375 is advanced until the distal end of the distal portion of the tubular member 375 contacts the proximal end of the proximal portion of tubular member 370 such that the proximal end of the proximal portion of tubular member 370 is spaced from distal end of the distal portion of tubular member 375 by portion 372a of conductor 256. In one embodiment, tubular member 375 is positioned relative to the conductive element 374 such that at least one end (e.g., the distal end in FIG. 31) of the tubular member 375 is at or near a point half-way along a length of conductive element 374. In other embodiments, at least one end of the tubular member 375 is at a different point along the length of conductive element 374, including points more proximal and more distal than the half-way point.

Figure 32:
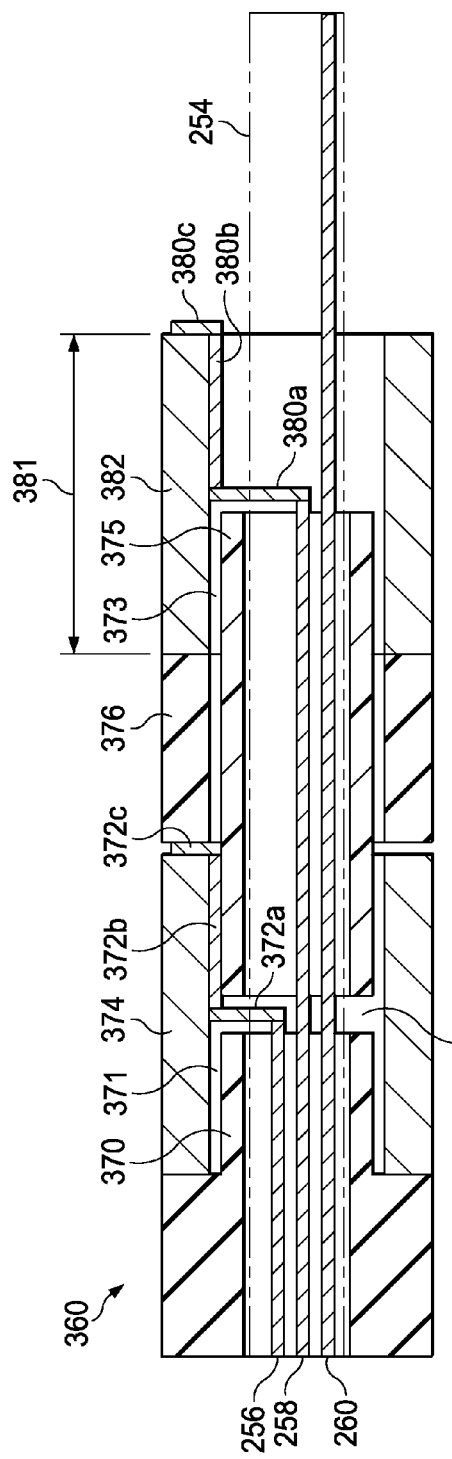

Referring now to FIG. 32, a conductive element 382 is positioned around the tubular member 375. In some embodiments, the conductive element 382 is advanced distally along the tubular member 375 until the conductive element 382 is positioned adjacent the proximal end of an insulating portion 376. The conductive element 382 may be positioned with a space 373 between it and the tubular member 375. The space 373 may be sized such that a portion of a conductor (such as conductor 256, 258, 260) may extend longitudinally between tubular member 375 and conductive element 382. As discussed herein, the space 373 may be filled with an adhesive or other suitable filling material when conductive element 382 is initially positioned and/or when one or more additional components of insulating member 360 are positioned. In one embodiment, tubular member 375 is positioned relative to the conductive element 374 such that at least one end (e.g., the proximal end in FIG. 32) of the tubular member 375 is at or near a point half-way along a length of conductive element 382. In other embodiments, at least one end of the tubular member 375 is at a different point along the length of conductive element 382, including points more proximal and more distal than the half-way point.

A portion 380a of the conductor 258 is advanced through an opening in the tubular member 375. The opening may be similar to one or more of openings 319, 336, 356, and 366 discussed above. In other embodiments, the tubular member 375 does not include an opening in the sidewall. Instead, the portion 380a extends out of a proximal end of the tubular member 375 and a separate tubular member is then abutted against portion 380a and the proximal end of the tubular member 375. A proximal end or a distal end of a tubular member may be described as an opening. In such embodiments, tubular member 375 may not have an opening or slot in the wall thereof to allow portion 380(a) to advance through and out of the tubular members 375. Instead, portion 380(a) may advance via a space 386 (FIG. 33) between adjacent tubular members (e.g., tubular members 375, 385 of FIG. 33). In some instances, the portion 380a is advanced out of tubular member 375 at or near a point half-way along a length 381 of conductive element 374. In other instances, the portion 380a is advanced at a different point along the length 381 of conductive element 374, including points more proximal and more distal than the half-way point. In that regard, the positioning of the opening and/or the size of the tubular member 375 is configured to allow the portion 380a to be advanced radially outward at a desired location relative to the conductive element 382. In some embodiments, the portion 380a of the conductor 258 is wrapped at least partially around the tubular member 375. A portion 380b of the conductor 258 is advanced longitudinally between the conductive element 382 and the tubular member 375 in space 373. In some embodiments, the portion 380b of the conductor 358 is wrapped at least partially around the tubular member 375. In other embodiments, portion 380b is advanced longitudinally without wrapping around tubular member 375 and/or the core, and extends along the length of the guidewire parallel to tubular member 375. A portion 380c of the conductor 258 is advanced from space 373 to a position adjacent to conductive element 382. According to an exemplary embodiment, portion 380b and/or portion 380c are routed partially under conductive band 382. A slot may be cut into some portion of the conductive band 382 (e.g., underneath, in the side of, etc.). Portion 380c may be received in the slot of the conductive band and soldered therein to the conductive band, which electrically couples conductor 258 and conductive band 382. Thus, portion 380c may be advanced radially outward to a position adjacent to the conductive band 382. In other embodiments, portion 380c may be advanced to a position adjacent the conductive band 382 without being received in a slot of the conductive band 382 (e.g., to a position between conductive band 382 and insulating member 384 of FIG. 33). In some embodiments, the portion 380c of the conductor 258 is wrapped at least partially around the tubular member 375. Advancing the portion 380b longitudinally in space 373 advantageously prevents short circuits that may occur if and when a conductive liquid infiltrates insulating member 376 (e.g., at a point where portion 380c is soldered or otherwise electrically coupled to conductive element 382). This is because a conductive liquid must travel along the distance that the portion 380b extends longitudinally in space 373 to reach the core.

The portion 380c of the conductor 258 extending through the opening of the tubular member 375 is electrically coupled to the conductive element 382. Any suitable techniques can be utilized to electrically couple the portion 380c of the conductor 258 to the conductive element 382, including soldering, laser welding, and/or other suitable technique. In some instances, the wrapping of the portion 380c of the conductor 258 around the tubular member 375 and/or removing a portion of an insulating layer or sheath is at least partially performed after the conductive element 382 is positioned around the tubular member 375.

Wrapping the conductor 258 at least partially around the tubular member 375 allows the soldering or other electrically coupling can be performed away from the opening of the tubular member 375. In some instances, one or more of portions 380a, 380b, 380c are wrapped around the tubular member 370 between about 90 degrees and about 270 degrees. In other instances, portions 380a, 380b, and 380c are not wrapped around tubular member 370. As an example, in some implementations the portion 380c of the conductor 258 is wrapped around the tubular member such that the conductor 258 can be soldered or otherwise electrically coupled to a conductive element positioned adjacent to and proximal to the portion 380c on an opposite of the tubular member 375 from the opening of the tubular member. Further, in embodiments where the conductor 258 includes an insulating layer or sheath around a conductive core, a section of the insulating layer is removed to expose a section of the conductive core. In that regard, it is understood that a section of the portion 380c wrapped around the tubular member 375 includes an insulating layer or sheath in some instances, while the insulating layer or sheath around another section of the portion 380c is removed to expose the underlying conductive material.

Figure 33:
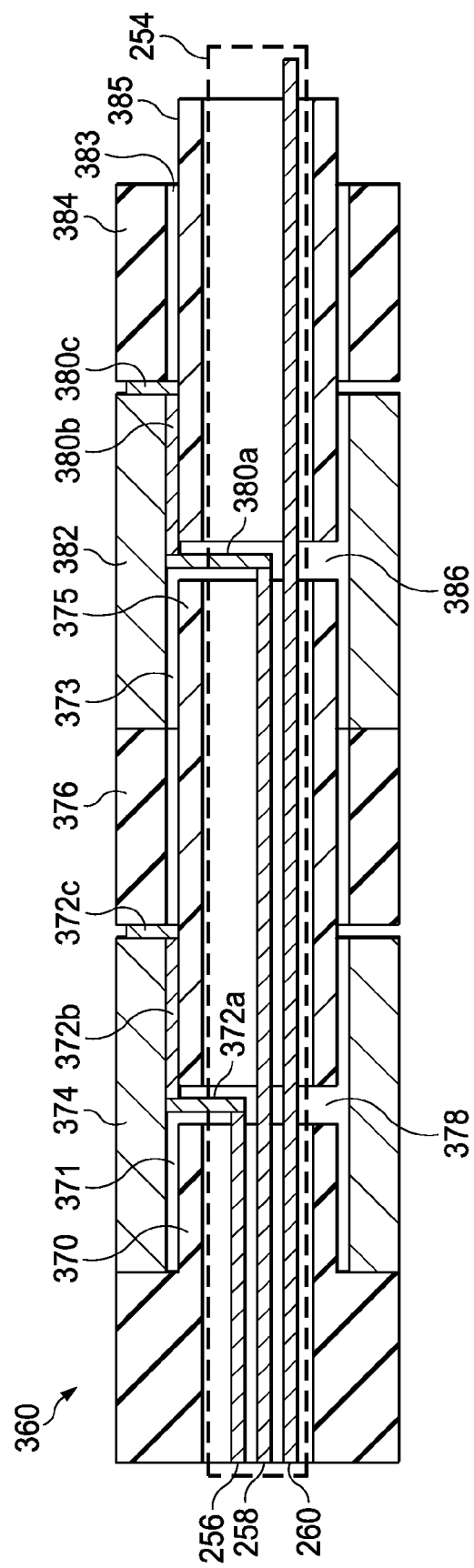

Referring now to FIG. 33, an insulating member 384 is positioned around a core 254 and conductor 260. The insulating member 384 is positioned coaxially around the core 254. In some embodiments, insulating member 384 and tubular member 385 are separate elements. For example, tubular member 385 may be positioned around core 254 and conductors 260 first and thereafter, insulating member 384 maybe positioned around tubular member 385. The insulating member 384 may be positioned with a space 383 between it and the tubular member 385. The space 383 may be sized such that a portion of a conductor (such as conductor 256, 258, 260) may extend longitudinally between tubular member 385 and insulating member 384. As discussed herein, the space 383 may be filled with an adhesive or other suitable filling material when insulating member 384 is initially positioned and/or when one or more additional components of insulating member 360 are positioned. In other embodiments, insulating member 384 and tubular member 385 are integrally formed and are not separate elements. In such embodiments, no space may be disposed between insulating member 384 and tubular member 385. However, a space may still be disposed between tubular member 385 and adjacent conductive elements 382 (e.g., space 373) and any more proximal conductive elements.

In other embodiments, the core 254 is offset with respect to a central longitudinal axis of the insulating member 384. In some embodiments, the insulating member 384 is identical or similar to one or more of the embodiments described above with respect to FIG. 21, 22, 25, 27, or 28. In the illustrated embodiment, insulating member 384 is similar to insulating member 330 of FIG. 25. The insulating member 384 is advanced distally over the core 254 until an insulating portion of the insulating member 384 is positioned adjacent to a proximal end of the conductive element 382. In some instances, the insulating member 384 is advanced distally along the core 254 until a distal end of the insulating portion of the insulating member 384 contacts a proximal end of the conductive element 382. In that regard, in some instances the insulating member 384 is advanced until it contacts the portion 380c of the conductor 258 such that the insulating member 384 is spaced from the conductive element 382 by portion 380c.

In the illustrated embodiment, a distal portion of the tubular member 385 extends within conductive element 382. As shown, the distal end of the distal portion of the tubular member 385 is spaced from the proximal end of the proximal portion of tubular member 375, represented by space 386. Generally, the length of space 386 along the longitudinal axis of the core 254 is between about 0.127 mm (0.005") and about 5.08 mm (0.20"), with some particular embodiments having lengths of 1.27 mm (0.050"), 2.54 mm (0.10"), and 3.81 mm (0.150"). In that regard, the length of space 386 is representative of the distance between the distal end of the distal portion of the tubular member 385 and the proximal end of the proximal portion of tubular member 375. In some instances, there is no space between the distal end of the distal portion of the tubular member 385 and the proximal end of the proximal portion of tubular member 375. In other words, the tubular member 385 is advanced until the distal end of the distal portion of the tubular member 385 contacts the proximal end of the proximal portion of tubular member 375 such that the proximal end of the proximal portion of tubular member 375 is apart from distal end of the distal portion of insulating member 385 by portion 380a of conductor 258. In one embodiment, tubular member 385 is positioned relative to the conductive element 382 such that at least one end (e.g., the distal end in FIG. 33) of the tubular member 385 is at or near a point half-way along a length of conductive element 382. In other embodiments, at least one end of the tubular member 385 is at a different point along the length of conductive element 382, including points more proximal and more distal than the half-way point.

Figure 34:
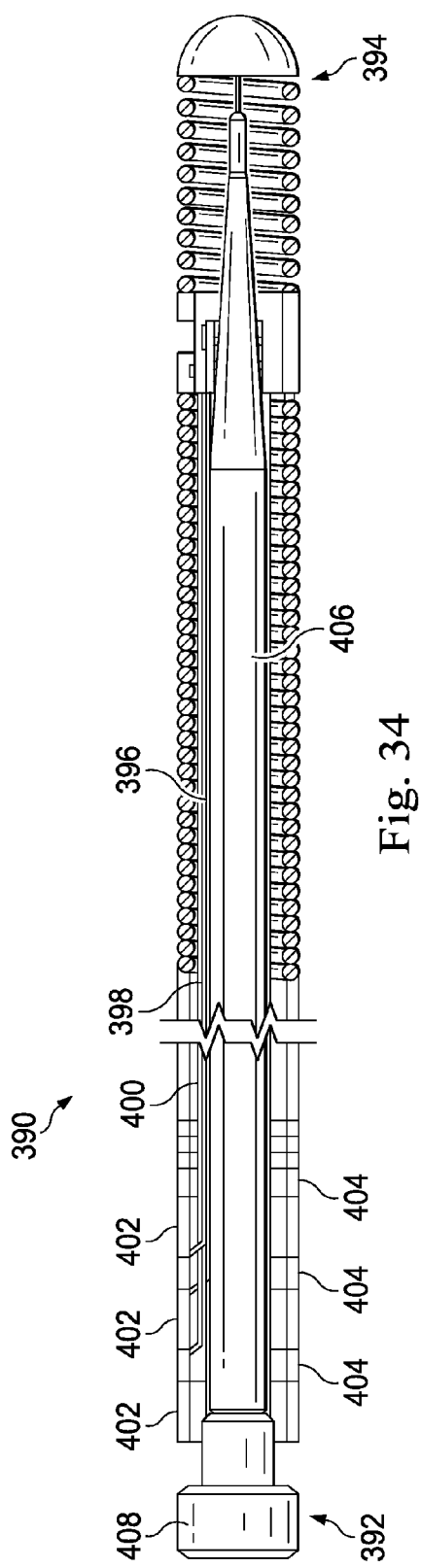
FIG. 34 is a diagrammatic side view of an intravascular device of the intravascular system of FIG. 1, according to an embodiment of the present disclosure.

Steps similar to those described in FIGS. 32-34 can be repeated to electrically couple additional conductive elements to the plurality of conductors extending along the core wire for any number of conductors and/or conductive elements. In some embodiments, an insulating member having a single tubular portion integrally formed with an insulating portion is utilized adjacent the proximal most conductive element. In that regard, in some instances, the tubular portion is arranged distally of the insulating portion, such that the tubular portion extends within the proximal most conductive element and the insulating portion serves as a proximal boundary of the connector portion. Further, in some embodiments, multiple conductors of the plurality of conductors are coupled to a single conductive element.

Referring to FIG. 34, a diagrammatic side view of an intravascular device of the intravascular system of FIG. 1 is shown, according to an embodiment of the present disclosure. Intravascular device 390 includes a proximal portion 392 (on the left side of FIG. 34) and distal portion 394 (on the right side of FIG. 34). As described herein, intravascular device 390 may include a flexible elongate member (the length of which is represented by the break in FIG. 34) including one or more components (e.g., electronic, optical, or electro-optical) positioned at the distal portion 394 of intravascular device 390.

Figure 35:
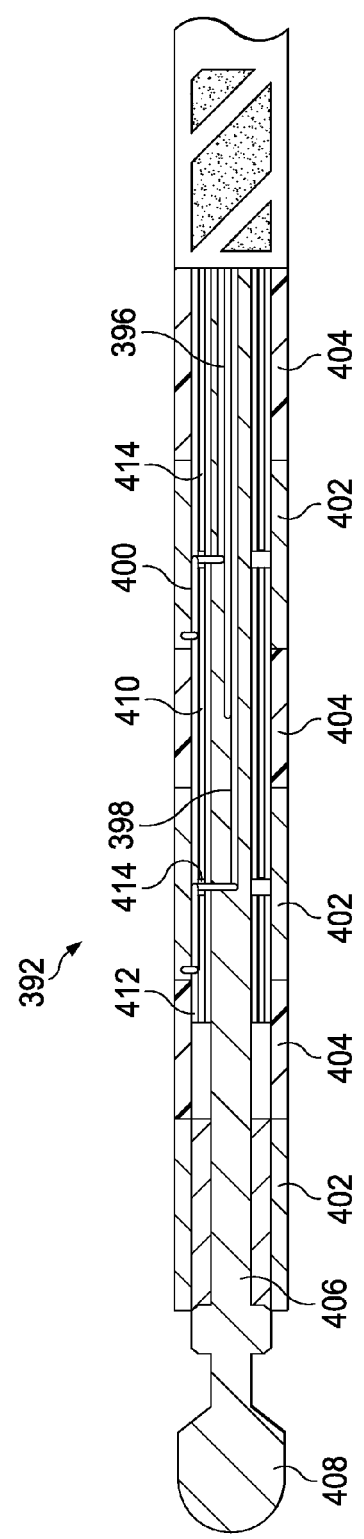
FIG. 35 is a diagrammatic cross-sectional side view of a proximal connector portion of the intravascular device of FIG. 34.

Referring to FIG. 35, a diagrammatic cross-sectional side view of a proximal connector portion of intravascular device is shown, according to an embodiment of the present disclosure. FIG. 35 may be a more detailed view of the proximal portion 392 of FIG. 34. Referring to both FIGS. 34 and 35, proximal portion 392 includes a locking core 408, which may be received in a connector (e.g., connector 104) of an intravascular system. In some embodiments, locking core 408 integrally formed with core wire 406, while in other embodiments, locking core 408 and core wire 406 are separate elements. Core wire 406 may extend substantially along an entire length of intravascular device 390. Conductors 396, 398, 400 may also extend substantially along an entire length of intravascular device 390. A sleeve 410 may be coaxially positioned around core wire 406 and conductors 396, 398, 400. Sleeve 410 may be formed of a polymer or polymide material. Sleeve 410 may be substantially similar to one or more tubular members described herein. In some embodiments, sleeve 410 includes a plurality of separate components, e.g., spaced apart from each other by spaces 414. In other embodiments, spaces 414 represent openings or slots in sleeve 410. One or more of conductors 396, 398, 400 may advance through space 414 (e.g., out of an end of one component forming sleeve 414 or out of a slot in sleeve 414). One or more of conductors 396, 398, 400 may extend longitudinally between the sleeve and conductive members 402. One or more of conductors 396, 398, 400 may be advanced (e.g., radially outward) to a position adjacent to conductive band 402. In that regard, proximal portion 392 includes a plurality of conductive bands 402 spaced apart from each other by insulating members 404. Insulating members 404 may be formed of a polymer or polymide material. Conductors 396, 398, 400 may be electrically coupled to one or more conductive bands 402. Spaces otherwise unoccupied within proximal portion 392 and intravascular device 390, such as space 412 may be filled with an adhesive.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of assembling an intravascular device, comprising:
    positioning a tubular member around a plurality of conductors and a core member such that the plurality of conductors and the core member are at least partially positioned within a lumen of the tubular member, the tubular member including an opening extending along a length of the tubular member in communication with the lumen, wherein a first portion of the tubular member has a first diameter and a second portion of the tubular member has a second diameter less than the first diameter;
    positioning a first conductive member around the tubular member;
    advancing a first of the plurality of conductors through the opening of the tubular member, longitudinally between the tubular member and the first conductive member, and through to a position adjacent to the first conductive member;
    electrically coupling the first of the plurality of conductors to the first conductive member;
    positioning a first insulating member around the tubular member adjacent to the first conductive member, the first insulating member comprising a first outer surface and a first plurality of projections extending radially from the first outer surface;
    positioning a second conductive member around the tubular member adjacent to the first insulating member such that the first insulating member is positioned between the first and second conductive members; and
    electrically coupling a second of the plurality of conductors to the second conductive member.

2. The method of claim 1, further comprising advancing the second of the plurality of conductors through the opening of the tubular member, longitudinally between the tubular member and the second conductive member, and through to a position adjacent to the second conductive member.

3. The method of claim 1, further comprising:
    positioning a second insulating member around the tubular member adjacent to the second conductive member, the second insulating member comprising a second outer surface and a second plurality of projections extending radially from the second outer surface;
    positioning a third conductive member around the tubular member adjacent to the second insulating member such that the second insulating member is positioned between the second and third conductive members; and
    electrically coupling a third of the plurality of conductors to the third conductive member.

4. The method of claim 1, wherein advancing the first of the plurality of conductors includes wrapping a portion of the first of the plurality of conductors around an outer surface of the tubular member.

5. The method of claim 4, wherein the first of the plurality of conductors is electrically coupled to the first conductive member adjacent a portion of the outer surface opposite from the opening of the tubular member.

6. The method of claim 5, wherein electrically coupling the first of the plurality of conductors to the first conductive member comprises soldering.

7. The method of claim 1, wherein the opening extends along an entire length of the tubular member.

8. The method of claim 1, wherein the opening extends along only a portion of the length of the tubular member.

9. The method of claim 1, wherein positioning the first conductive member around the tubular member comprises positioning the first conductive member around the second portion of the tubular member.

10. The method of claim 9, wherein the opening extends along the second portion of the tubular member.

11. A method of assembling an intravascular device, comprising:
   positioning a first tubular member around a plurality of conductors and a core member such that the plurality of conductors and the core member are at least partially positioned within a lumen of the first tubular member, the first tubular member including an opening extending along a length of the first tubular member in communication with the lumen;
   positioning a first conductive member around the first tubular member;
   advancing a first of the plurality of conductors through the opening of the first tubular member, longitudinally between the first tubular member and the first conductive member, and through to a position adjacent to the first conductive member;
   electrically coupling the first of the plurality of conductors to the first conductive member; and
   positioning a second tubular member around the plurality of conductors, less the first of the plurality of conductors, and the core member such that the plurality of conductors, less the first of the plurality of conductors, and the core member are at least partially positioned within a lumen of the second tubular member, wherein a first portion of the second tubular member has a first diameter, a second portion of the second tubular member has a second diameter less than the first diameter, and a third portion of the second tubular member has a third diameter less than the first diameter.

12. The method of claim 11, wherein the second tubular member is positioned around the plurality of conductors, less the first of the plurality of conductors, and the core member such that the third portion of the second tubular member is positioned at least partially within the first conductive member.

13. The method of claim 11, further comprising positioning a second conductive member around the second portion of the second tubular member such that the first portion of the second tubular member is positioned between the first conductive member and the second conductive member.

14. The method of claim 13, further comprising electrically coupling a second of the plurality of conductors to the second conductive member.

15. The method of claim 14, further comprising advancing the second of the plurality of conductors through an opening extending along a length of the second tubular member in communication with the lumen of the second tubular member, longitudinally between the second tubular member and the second conductive member, and through to a position adjacent to the second conductive member.

16. An intravascular device, comprising:
   a first tubular member positioned around a plurality of conductors and a core member such that the plurality of conductors and the core member are at least partially positioned within a lumen of the first tubular member;
   a first conductive member positioned around the first tubular member, wherein a first of the plurality of conductors is electrically coupled to the first conductive member and extends longitudinally between the first tubular member and the first conductive member and through to a position adjacent to the first conductive member;
   a first insulating member positioned adjacent to the first conductive member; and
   a second conductive member positioned adjacent to the first insulating member such that the first insulating member is positioned between the first and second conductive members, wherein a second of the plurality of conductors is electrically coupled to the second conductive member,
   wherein the second of the plurality of conductors extends longitudinally between a second tubular member and the second conductive member and through to a position adjacent to the second conductive member.

17. The intravascular device of claim 16, wherein the second tubular member is positioned proximal of the first tubular member such that a first opening is defined between the first and second tubular members, and wherein the first of the plurality of conductors extends through the first opening.

18. The intravascular device of claim 17, wherein the first opening is positioned adjacent a midpoint of the first conductive member.

19. The intravascular device of claim 16, further comprising a second insulating member positioned around the second tubular member adjacent to the second conductive member.

20. The intravascular device of claim 19, further comprising a third conductive member positioned around the second tubular member adjacent to the second insulating member such that the second insulating member is positioned between the second and third conductive members.

21. The intravascular device of claim 20, wherein a third of the plurality of conductors is electrically coupled to the third conductive member.

22. The intravascular device of claim 20, wherein the third conductive member is electrically coupled to the core member.

23. An intravascular device, comprising:
   a first tubular member positioned around a plurality of conductors and a core member such that the plurality of conductors and the core member are at least partially positioned within a lumen of the first tubular member;
   a second tubular member positioned adjacent to but spaced from the first tubular member such that a first opening is defined between the first and second tubular members; and
   a first conductive member positioned around at least a portion of the first tubular member and at least a portion of the second tubular member, wherein a first of the plurality of conductors is electrically coupled to the first conductive member and extends from the lumen of the first tubular member through the first opening, longitudinally between the second tubular member and the first conductive member, and through to a position adjacent an end portion of the first conductive member.

24. The intravascular device of claim 23, wherein the first opening is positioned at or near a midpoint of the first conductive member.

* * * * *